United States Patent [19]

Kim

[11] Patent Number: 5,797,920
[45] Date of Patent: Aug. 25, 1998

[54] CATHETER APPARATUS AND METHOD USING A SHAPE-MEMORY ALLOY CUFF FOR CREATING A BYPASS GRAFT IN-VIVO

[75] Inventor: Ducksoo Kim, Dover, Mass.

[73] Assignee: Beth Israel Deaconess Medical Center, Boston, Mass.

[21] Appl. No.: 702,068

[22] Filed: Aug. 23, 1996

Related U.S. Application Data

[63] Continuation-in-part of Ser. No. 664,165, Jun. 14, 1996, Pat. No. 5,676,670.

[51] Int. Cl.$^6$ ........................................ A61F 11/00
[52] U.S. Cl. .................. 606/108; 606/185; 606/195; 604/164; 623/12
[58] Field of Search ...................... 606/108, 159, 606/184, 185, 192, 198, 195; 604/164, 161; 623/1, 12

[56] References Cited

U.S. PATENT DOCUMENTS

| | | | |
|---|---|---|---|
| 4,769,031 | 9/1988 | McGough et al. | 623/1 |
| 4,969,890 | 11/1990 | Sugita et al. | 623/1 |
| 5,254,105 | 10/1993 | Haaga | 606/108 |
| 5,332,402 | 7/1994 | Teitelbaum | 623/2 |
| 5,431,661 | 7/1995 | Koch | 606/108 |
| 5,431,676 | 7/1995 | Dubrul et al. | 606/191 |
| 5,540,713 | 7/1996 | Schnepp-Pesch et al. | 606/198 |
| 5,571,167 | 11/1996 | Maginot | 623/1 |
| 5,571,170 | 11/1996 | Palmaz et al. | 623/12 |
| 5,571,173 | 11/1996 | Parodi | 623/12 |

*Primary Examiner*—Robert A. Hafer
*Assistant Examiner*—J. Yu
*Attorney, Agent, or Firm*—David Prashker

[57] ABSTRACT

The present invention provides a catheter apparatus, an introducer system, and a methodology for creating a bypass on-demand between an unobstructed blood vessel such as the aorta and an obstructed blood vessel such as an obstructed coronary artery in-vivo using a shaped memory alloy cuff and a graft segment in tandem as a shunt. The invention allows the placement and creation of single or multiple bypass grafts without use of a heart-lung machine and without need for stopping the heart of the patient during the coronary artery bypass surgery.

12 Claims, 26 Drawing Sheets

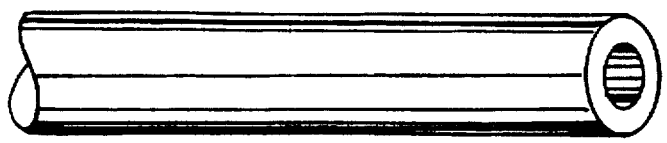 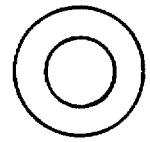
FIG. 3A        FIG. 3B
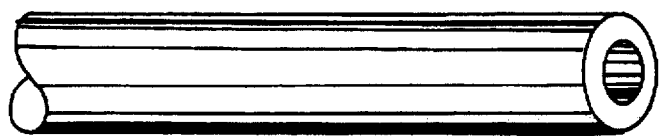 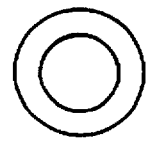
FIG. 4A        FIG. 4B
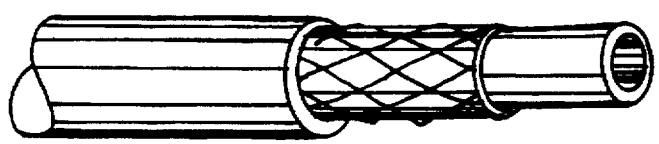 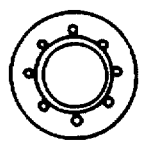
FIG. 5A        FIG. 5B
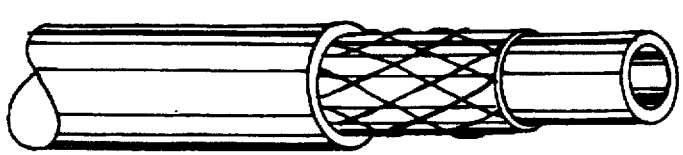 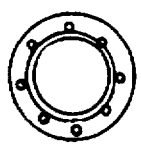
FIG. 6A        FIG. 6B

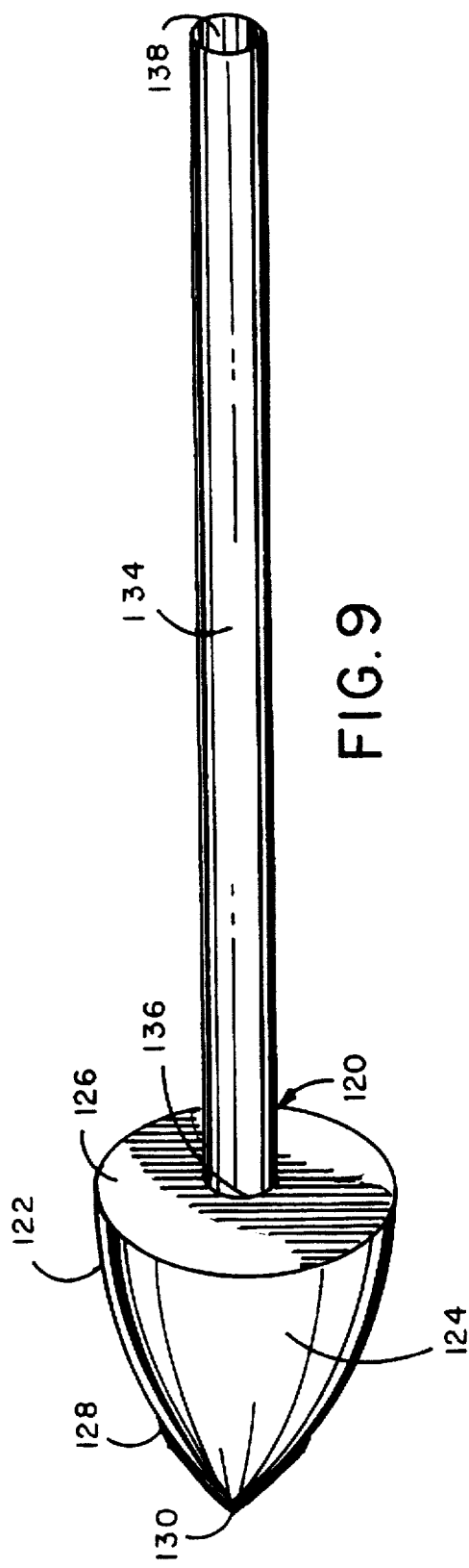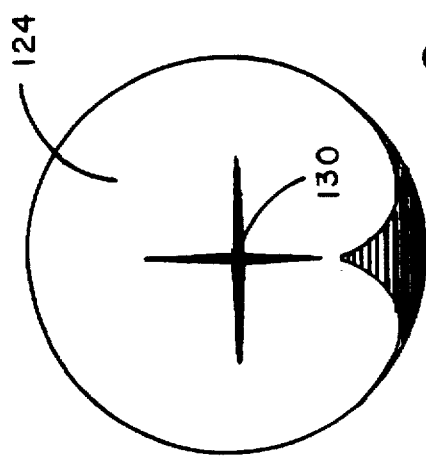

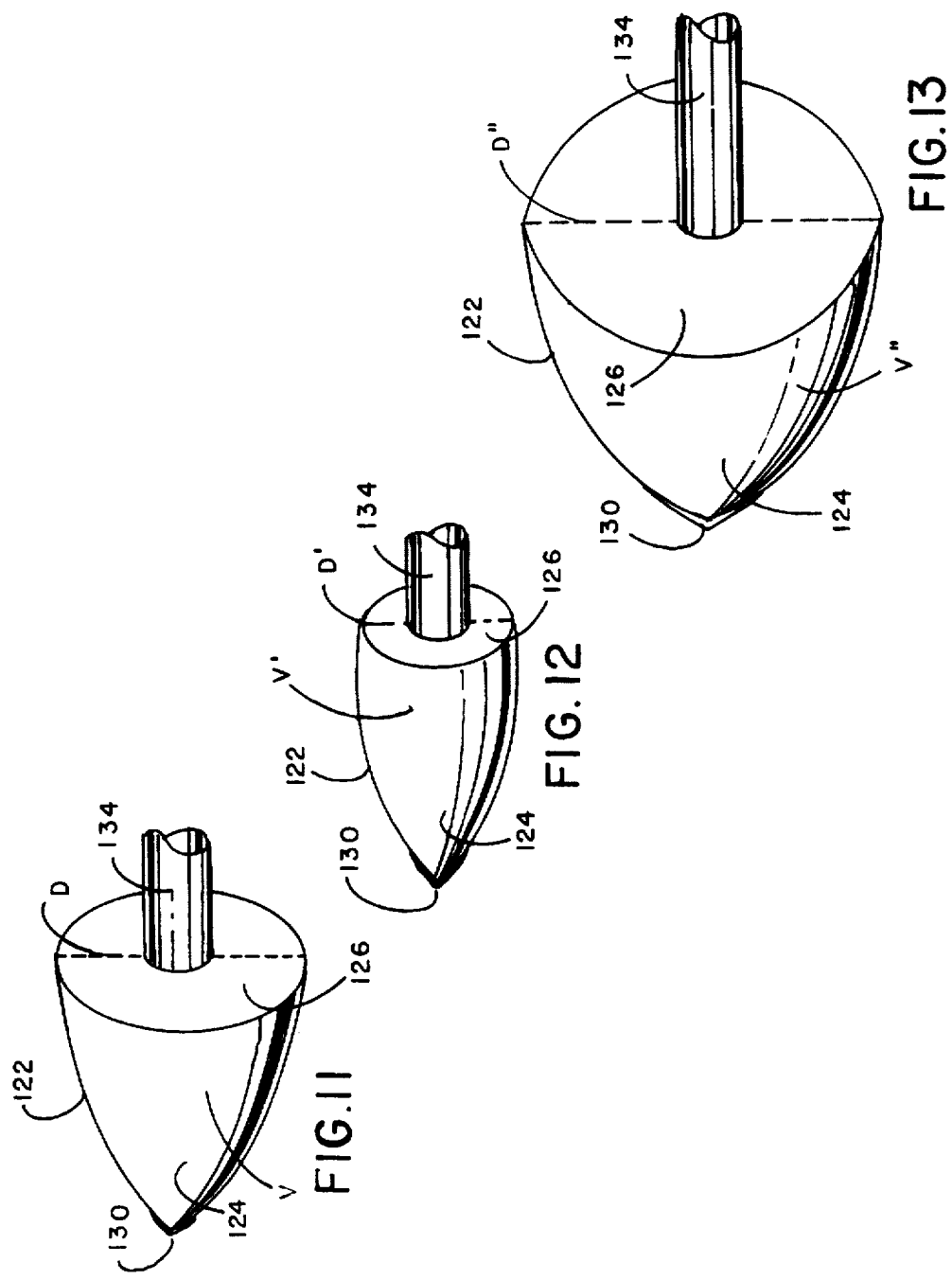

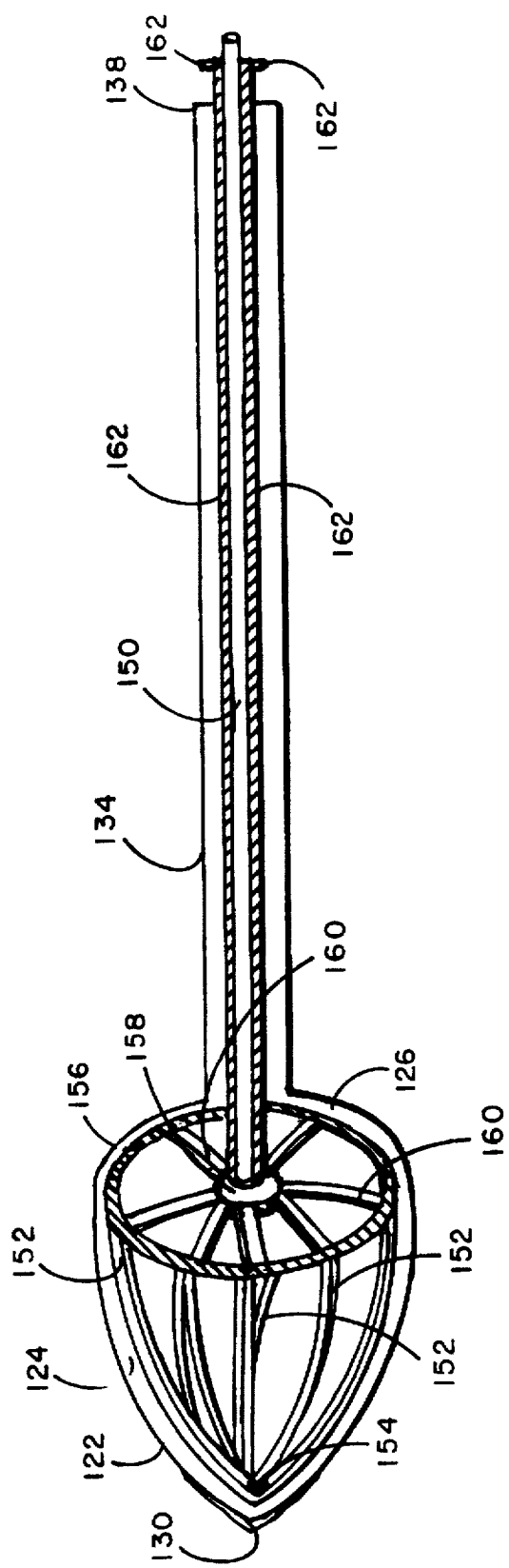

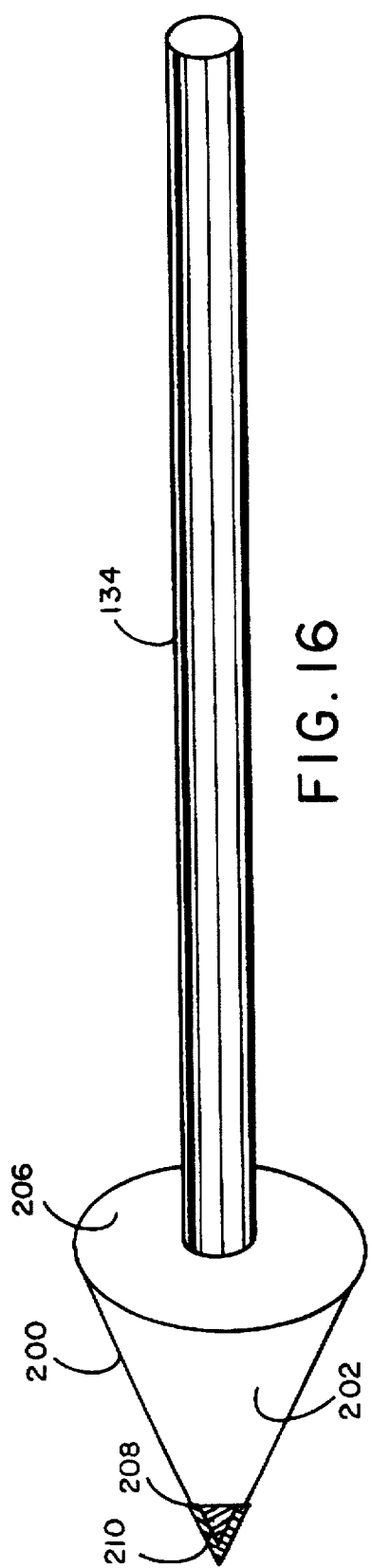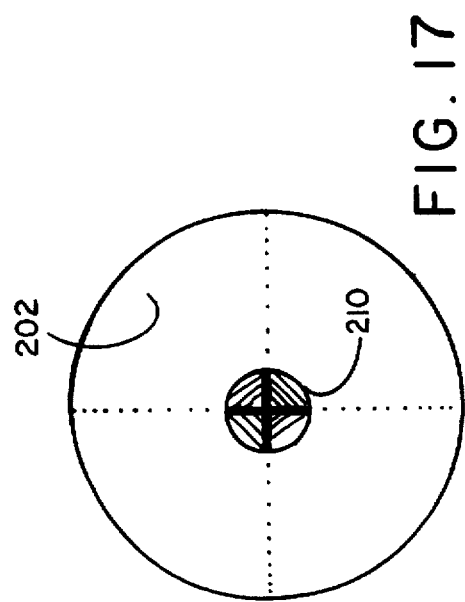

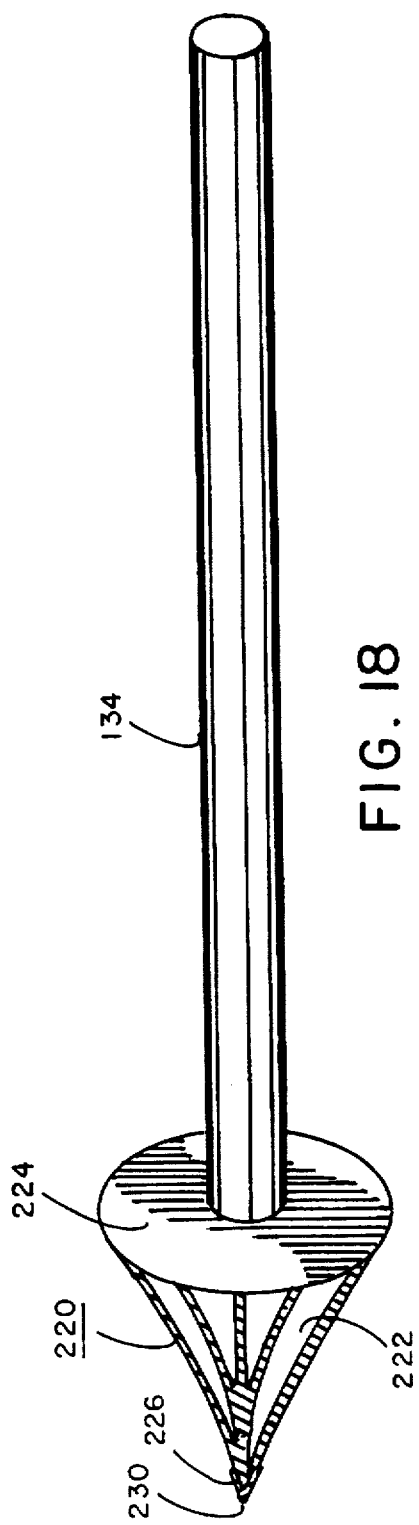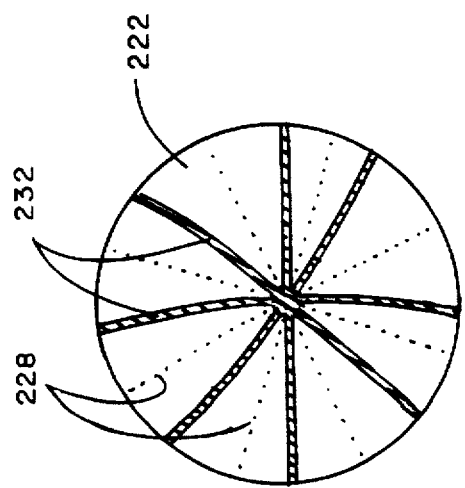
FIG. 18
FIG. 19

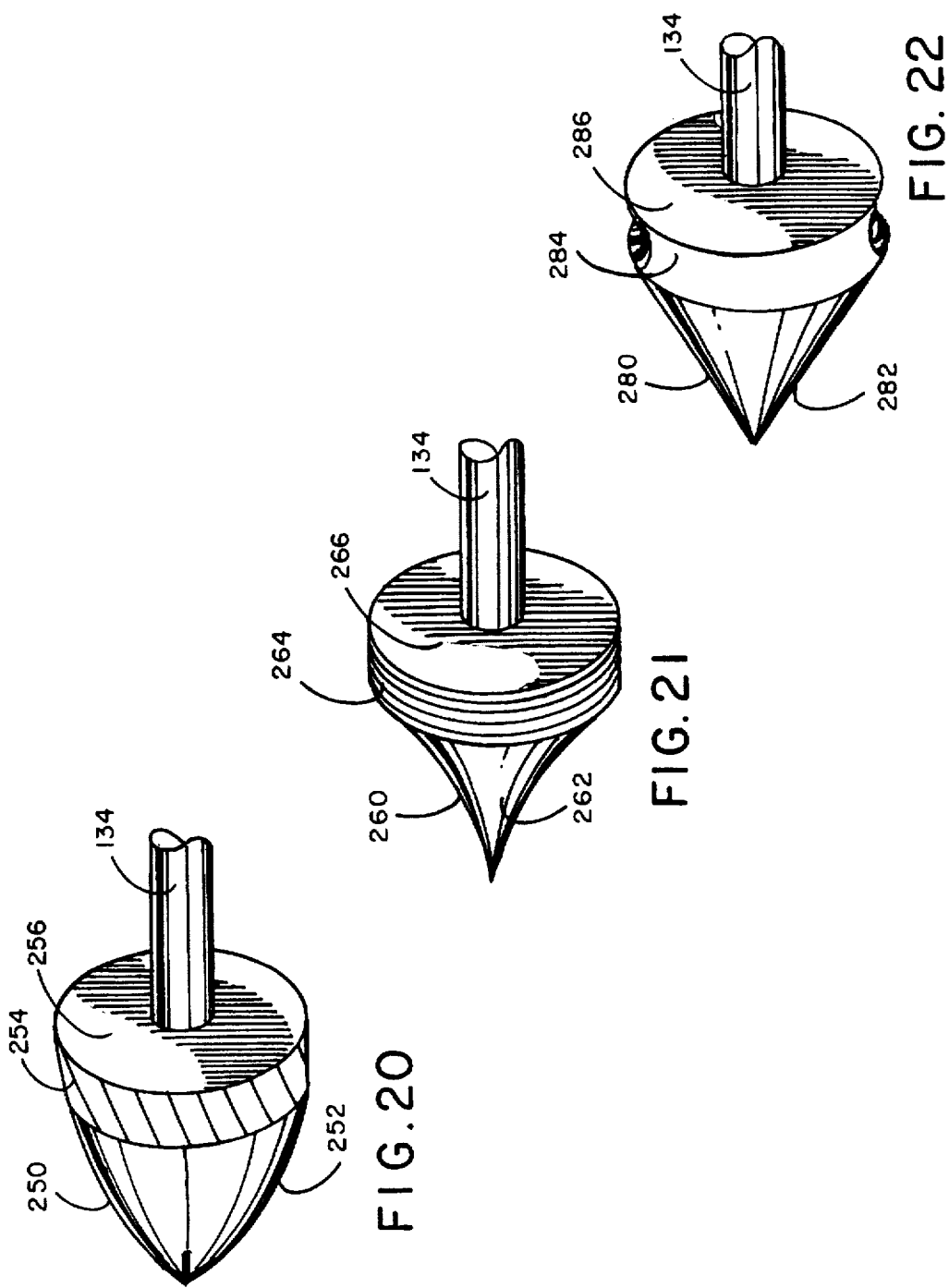

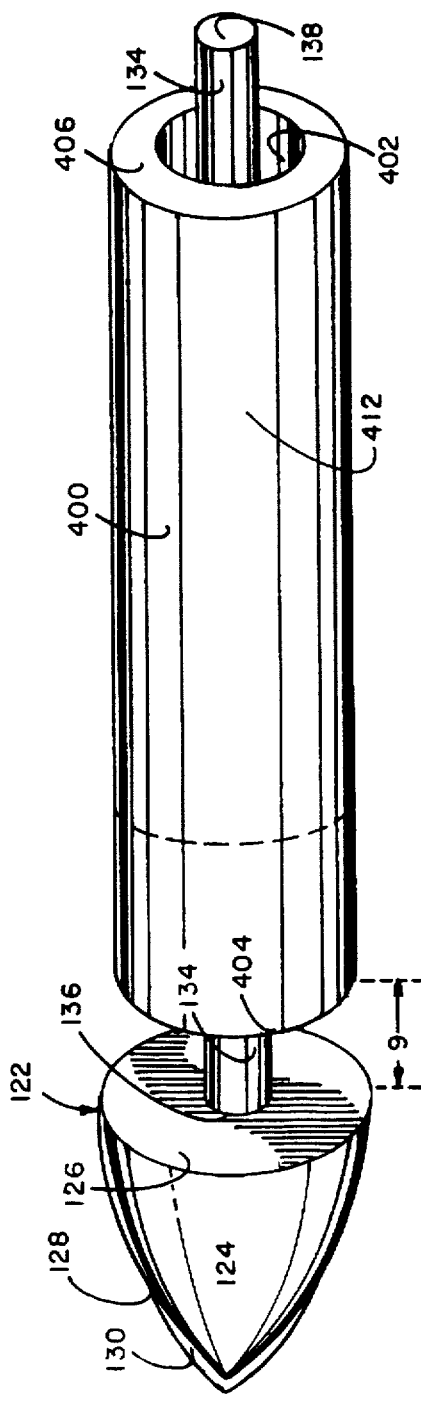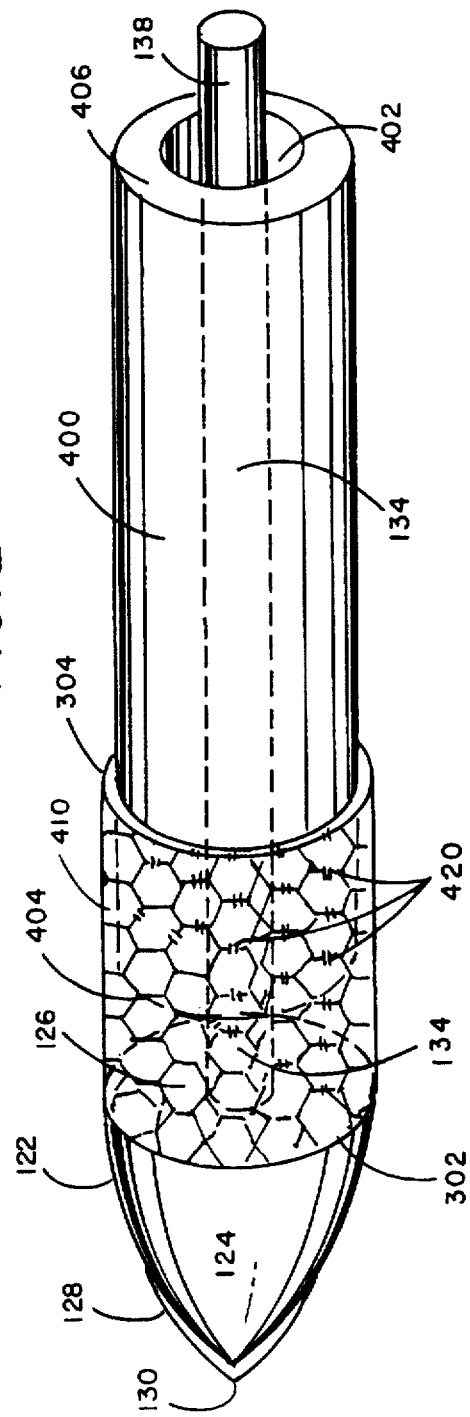
FIG. 27
FIG. 28

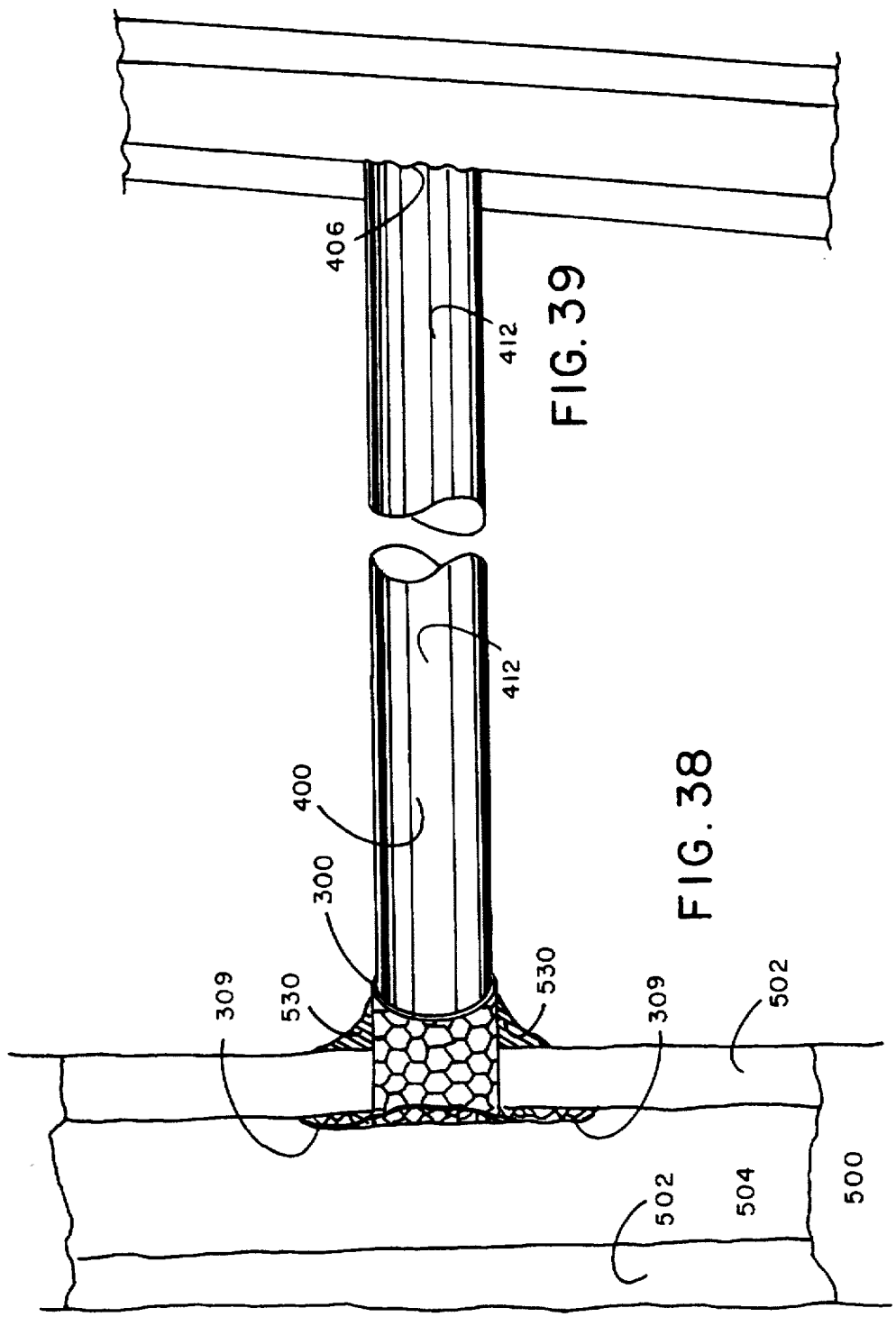

CATHETER APPARATUS AND METHOD USING A SHAPE-MEMORY ALLOY CUFF FOR CREATING A BYPASS GRAFT IN-VIVO

CROSS REFERENCE

The present application is a Continuation-In-Part of U.S. patent application Ser. No. 664,165 filed Jun. 14, 1996, now U.S. Pat. No. 5,676,670.

FIELD OF THE INVENTION

The present invention is concerned generally with minimally invasive vascular bypass surgery; and is directed to a catheterization methodology for creating a vascular bypass between an unobstructed artery or vein and an obstructed artery or vein in-vivo.

BACKGROUND OF THE INVENTION

Coronary artery disease is the single leading cause of human mortality and is annually responsible for over 900,000 deaths in the United States alone. Additionally, over 3 million Americans suffer chest pain (angina pectoris) because of it. Typically, the coronary artery becomes narrowed over time by the build up of fat, cholesterol and blood clots. This narrowing of the artery is called arteriosclerosis; and this condition slows the blood flow to the heart muscle (myocardium) and leads to angina pectoris due to a lack of nutrients and adequate oxygen supply. Sometimes it can also completely stop the blood flow to the heart causing permanent damage to the myocardium, the so-called "heart attack."

The conventional treatment procedures for coronary artery disease vary with the severity of the condition. If the coronary artery disease is mild, it is first treated with diet and exercise. If this first course of treatment is not effective, then the condition is treated with medications. However, even with medications, if chest pain persists (which is usually secondary to development of serious coronary artery disease), the condition is often treated with invasive procedures to improve blood flow to the heart. Currently, there are several types of invasive procedures: (1) Catheterization techniques by which cardiologists use balloon catheters, atherectomy devices or stents to reopen up the blockage of coronary arteries; or (2) Surgical bypass techniques by which surgeons surgically place a graft obtained from a section of artery or vein removed from other parts of the body to bypass the blockage.

Conventionally, before the invasive procedures are begun, coronary artery angiography is usually performed to evaluate the extent and severity of the coronary artery blockages. Cardiologists or radiologists thread a thin catheter through an artery in the leg or arm to engage the coronary arteries. X-ray dye (contrast medium) is then injected into the coronary artery through a portal in the catheter, which makes the coronary arteries visible under X-ray, so that the position and size of the blockages in the coronary arteries can be identified. Each year in U.S.A., more than one million individuals with angina pectoris or heart attack undergo coronary angiographies for evaluation of such coronary artery blockages. Once the blocked arteries are identified, the physician and surgeons then decide upon the best method to treat them.

One of the medically accepted ways to deal with coronary arterial blockage is percutaneous transluminal coronary angioplasty (PTCA). In this procedure, cardiologists thread a balloon catheter into the blocked coronary artery and stretch it by inflating the balloon against the arterial plaques causing vascular blockage. The PTCA procedure immediately improves blood flow in the coronary arteries, relieves angina pectoris, and prevents heart attacks. Approximately 400,000 patients undergo PTCA each year in the U.S. However, when the arterial blockages are severe or widespread, the angioplasty procedure may fail or cannot be performed. In these instances, coronary artery bypass graft (CABG) surgery is then typically performed. In such bypass surgery, surgeons typically harvest healthy blood vessels from another part of the body and use them as vascular grafts to bypass the blocked coronary arteries. Each vascular graft is surgically attached with one of its ends joined to the aorta and the other end joined to the coronary artery. Approximately 500,000 CABG operations are currently performed in the U.S. each year to relieve symptoms and improve survival from heart attack.

It is useful here to understand in depth what a coronary arterial bypass entails and demands both for the patient and for the cardiac surgeon. In a standard coronary bypass operation, the surgeon must first make a foot-long incision in the chest and split the breast bone of the patient. The operation requires the use of a heart-lung machine that keeps the blood circulating while the heart is being stopped and the surgeon places and attaches the bypass grafts. To stop the heart, the coronary arteries also have to be perfused with a cold potassium solution (cardioplegia). In addition, the body temperature of the patient is lowered by cooling the blood as it circulates through the heart-lung machine in order to preserve the heart and other vital organs. Then, as the heart is stopped and a heart-lung machine pumps oxygenated blood through the patient's body, the surgeon makes a tiny opening into the front wall of the target coronary artery with a very fine knife (arteriotomy); takes a previously excised saphenous vein (a vein from a leg) or an internal mammary artery (an artery from the chest); and sews the previously excised blood vessel to the coronary artery.

The most common blood vessel harvested for use as a graft is the greater (long) saphenous vein, which is a long straight vein running from just inside the ankle bone to the groin. The greater saphenous vein provides a bypass conduit of the most desired size, shape, and length for use with coronary arteries. The other blood vessel frequently used as a bypass graft is the left or right internal mammary artery, which comes off the subclavian artery and runs alongside the undersurface of the breastbone (sternum). Typically, the internal mammary artery remains attached to the subclavian artery proximally (its upper part) but is freed up distally (its lower part); and it is then anastomosed to the coronary artery. However, the saphenous vein graft should be sewn not only to coronary artery but also to the aorta, since the excised vein is detached at both ends. Then, to create the anastomosis at the aorta, the ascending thoracic aorta is first partially clamped using a curved vascular clamp to occlude the proper segment of the ascending aorta; and a hole is then created through the front wall of the aorta to anchor the vein graft with sutures. The graft bypasses the blockage in the coronary artery and restores adequate blood flow to the heart. After completion of the grafting, the patient is taken off of the heart-lung machine and the patient's heart starts beating again. Most of the patients can leave the hospital in about 6 days after the CABG procedure.

It will be noted that coronary artery bypass surgery is considered a more definitive method for treating coronary arterial disease because all kinds of obstructions cannot be treated by angioplasty; and because a recurrence of blockages in the coronary arteries even after angioplasty is not unusual. Also coronary artery bypass surgery usually provides for a longer patency of the grafts and the bypassed coronary arteries in comparison with the results of PTCA procedure. However, coronary artery bypass surgery is a far more complicated procedure, having need of a heart-lung machine and a stoppage of the heart. Also, it is clearly the more invasive procedure and is more expensive to perform than PTCA. Therefore, cardiac surgeons have recently developed an alternative to the standard bypass surgery, namely "minimally invasive bypass operation (MIBO) in order to reduce the risks and the cost associated with CABG surgery. Also, the MIBO is performed without use of a heart-lung machine or the stopping of the heart.

There are several ways that minimally invasive coronary bypass surgeries are being done today. Some versions are modeled after the video-assisted, fiber-optic techniques developed previously for gallbladder and other general surgeries. Other techniques have modified decades-old methods to sew arterial grafts onto beating hearts without using heart-lung machines. In the new and most popular version of the minimally invasive coronary bypass operation, surgeons use a thoracoscope, a fiber-optic device that is similar to a laparoscope. Initially, a three-inch incision is made to the left of the breast bone through which the surgeons operate. Three additional one-inch incisions then are made to insert a video camera, knife, surgical stapler, and other instruments. In the first stage of the operation, surgeons prepare the internal mammary artery, which courses vertically behind the rib cage, while watching on a video monitor. The internal mammary artery is freed up distally and is then sewn to the left anterior descending coronary artery. The internal mammary artery thus supplies blood to the coronary artery in place of blocked circulation of the heart. The wall of the chest formerly served by the mammary artery picks up blood from elsewhere via collateral blood circulations.

As a bypass graft, the left internal mammary artery (LIMA) offers a number of advantages to the coronary artery surgery including higher patency rate; and anatomically, histologically and geometrically provides a more comparable graft than the saphenous vein graft. LIMA is particularly useful as a graft to the coronary arteries such as the left anterior descending, diagonal branches, and ramus intermedius arteries (which are located on the surface of the heart relatively close to the left internal mammary artery). However, there are several disadvantages associated with a CABG operation with a left internal mammary artery graft, which are as follows: (1) technically, this artery is more tedious to take down; (2) sometimes the left internal mammary artery is inadequate in size and length; (3) the operation is suitable only for the five percent of candidates for coronary artery bypass because only a single left internal mammary artery is available as a graft; (4) anatomically, the operation is limited mainly to the left anterior descending coronary artery because of its location ad length; and (5) the majority of patients need more than single vessel bypass surgery.

In comparison, coronary arteries as small as 1 mm in diameter can be revascularized by vein grafting; and the saphenous vein is longer, larger, and more accessible than the left internal mammary artery. Equally important, although the greater or lesser saphenous veins of the leg are preferred, the cephalic or basilic veins in the arm are available as alternatives when the leg veins in the patient are unavailable or are unsuitable. For these reasons, the vein graft has today become the standard conduit for myocardial revascularization.

There remains, however, a long-standing and continuing need for a bypass technique which would allow surgeons to perform multiple bypass procedures using vein grafts as vascular shunts in a minimally invasive way; and, in particular, the need remains for a simpler method to place more than one vein graft proximally to the aorta and distally to the coronary artery without using a heart-lung machine and without stopping the heart. If such a technique were to be created, it would be recognized as a major advance in bypass surgery and be of substantial benefit and advantage for the patient suffering from coronary artery disease.

SUMMARY OF THE INVENTION

The present invention has multiple aspects. A first aspect is a catheter apparatus for creating a bypass on-demand between an unobstructed artery and an obstructed artery in-vivo using a graft segment as a conduit, said bypass catheter apparatus comprising:

a catheter suitable for introduction into and extension through the body in-vivo to a chosen site wherein an unobstructed artery is in anatomic proximity to an obstruction lying within another artery, said catheter being comprised of a hollow tube of fixed axial length having a discrete proximal end, a discrete distal end, and at least one internal lumen of predetermined diameter;

an obturator for on-demand introduction and passage through said catheter to a chosen site on the unobstructed artery in-vivo, said obturator comprising (1) an expandable and contractible puncturing headpiece for puncture of and entry into the lumen of an unobstructed artery, said puncturing headpiece being expandable on-demand to a size greater than the diameter of said internal lumen of said catheter and being contractible on-demand to a size less than the diameter of said internal lumen of said catheter, (2) a perforating end tip on said puncturing headpiece to facilitate the perforation of an arterial wall at the chosen site in-vivo (3) an elongated shaft of fixed axial length integrated with said puncturing headpiece, said elongated shaft being configured for the carrying and transport of the graft conduit within said internal lumen of said catheter to the chosen vascular site on the unobstructed artery in-vivo, (4) means for expanding and contracting said puncturing headpiece of said obturator on-demand; and a thermoelastic cuff for positioning over said elongated shaft adjacent to said puncturing headpiece of said obturator together with the graft conduit, said cuff being comprised of a deformable thermoelastic shape-memory alloy, a portion of said thermoelastic cuff being substantially in a first shaped configuration at temperatures less than about 25°–35° C. while deforming into a memory-shaped second configuration at temperatures greater than about 25°–35° C., (i) wherein, prior to the perforation of the unobstructed artery in-vivo by said puncturing headpiece of said obturator, at least a portion of said thermoelastic cuff in a first shaped configuration has been engaged and joined to one end of the graft segment then carried by said elongated shaft of said obturator, (ii) and wherein, after the perforation of the unobstructed artery in-vivo by said puncturing headpiece of said obturator, at least part of said engaged cuff is extended into the lumen of the unobstructed artery, is deformed in-situ into a memory-shaped second configuration, and said engaged cuff becomes attached via said deformation to the interior of the unobstructed artery, (iii) and whereby said cuff engaged end of the graft segment become secured to and placed in blood flow communication with the unobstructed artery and serves as conduit means for bypassing an obstruction and restoring arterial blood flow from the unobstructed artery to the obstructed artery.

A second aspect of the invention defines a catherization method for creating a bypass on-demand between an unobstructed artery and an obstructed artery in-vivo using a graft segment as a conduit, said bypass catheterization method comprising the steps of:

providing a catheter suitable for introduction into and extension through the body in-vivo to a chosen vascular site wherein an unobstructed artery is in anatomic proximity to an obstruction lying within another artery, said catheter being comprised of a hollow tube of fixed axial length having a discrete proximal end, a discrete distal end, and at least one internal lumen of predetermined diameter, providing an obturator for on-demand introduction and said catheter to a chosen site on the unobstructed artery in-vivo, said obturator comprising (1) an expandable and contractible puncturing headpiece for puncture of and entry into the lumen of an unobstructed artery, said puncturing headpiece being expandable on-demand to a size greater than the diameter of said internal lumen of said catheter and also being contractible on-demand to a size less than the diameter of said internal lumen of said catheter, (2) a perforating end tip on said puncturing headpiece to facilitate the perforation of an arterial wall at the chosen vascular site in-vivo (3) an elongated shaft of fixed axial length integrated with said puncturing headpiece, said elongated shaft being configured for the carrying and transport of a graft segment within said internal lumen of said catheter to the chosen site on the unobstructed artery in-vivo, (4) means for expanding and contracting said puncturing headpiece of said obturator on-demand;

placing a graft segment on the elongated shaft adjacent to said puncturing headpiece of said obturator;

positioning an undeformed thermoelastic cuff over said elongated shaft and one end of the graft segment lying adjacent to said puncturing headpiece of said obturator such that at least a portion of said undeformed thermoelastic cuff engages and is joined to an end of the graft segment, said cuff being comprised of a deformable thermoelastic shape-memory alloy, a portion of said thermoelastic cuff being substantially in a first shaped configuration at temperatures less than about 25°–35° C. while deforming into a memory-shaped second configuration at temperatures greater than about 25°–35° C.;

perforating the unobstructed artery at the chosen site in-vivo using said puncturing headpiece of said obturator;

extending at least part of said engaged thermoelastic cuff into the lumen of the unobstructed artery;

deforming said extended thermoelastic cuff in-situ into the memory-shaped second configuration;

(i) whereby said engaged cuff becomes attached via said deformation to the interior of the unobstructed artery, (ii) and whereby said cuff engaged end of the graft segment become secured to and placed in blood flow communication with the unobstructed artery; and joining the other end of the secured graft segment to the obstructed artery at a chosen site distal to the obstruction, said joined graft segment serving as a conduit means for bypassing the obstruction and restoring arterial blood flow from the unobstructed artery to the obstructed artery.

BRIEF DESCRIPTION OF THE FIGURES

The present invention may be more easily and completely understood when taken in conjunction with the accompanying drawing, in which:

FIGS. 3A and 3B are perspective and cross-sectional views of a single wall catheter tube of normal thickness;

FIGS. 4A and 4B are perspective and cross-sectional views of a single wall catheter tube of reduced thickness;

FIGS. 5A and 5B are perspective and cross-sectional views of a multiple-wall catheter tube of normal thickness;

FIGS. 6A and 6B are perspective and cross-sectional views of a multiple-wall catheter tube of reduced thickness;

FIG. 9 is a perspective view of a preferred first obturator;

FIG. 10 is a frontal view of the first obturator of FIG. 9;

FIG. 11 is a side view of the puncturing headpiece of the first obturator shown in FIG. 9;

FIG. 12 is a side view of the puncturing headpiece of FIG. 11 when in a contracted state;

FIG. 13 is a side view of the puncturing headpiece of FIG. 11 when in an expanded state;

FIG. 14 is an exposed view of a mechanical assembly used for expanding and contracting a puncturing headpiece on-demand in an obturator;

FIG. 16 is a perspective view of a second obturator;

FIG. 17 is a frontal view of the second obturator of FIG. 16;

FIG. 18 is a perspective view of a third obturator;

FIG. 19 is a frontal view of the third obturator of FIG. 18;

FIG. 20 is a side view of an alternative fourth puncturing headpiece of an obturator;

FIG. 21 is a side view of an alternative fifth puncturing headpiece of an obturator;

FIG. 22 is a side view of an alternative sixth puncturing headpiece of an obturator;

FIG. 27 is a perspective view of a previously excised vascular segment position on the elongated shaft of the preferred first obturator of FIG. 9;

FIG. 28 is a perspective view of the preferred first deformable cuff of FIG. 23A in combination with the previously excised vascular segment shown in FIG. 27;

FIG. 38 is a partially exposed view of the bypass conduit grafted and secured to the unobstructed blood vessel in-vivo; and FIG. 39 is a partially exposed view of the other open end of the bypass conduit anastomosed in the conventionally known manner to another obstructed blood vessel.

DETAILED DESCRIPTION OF THE INVENTION

Figure 1:
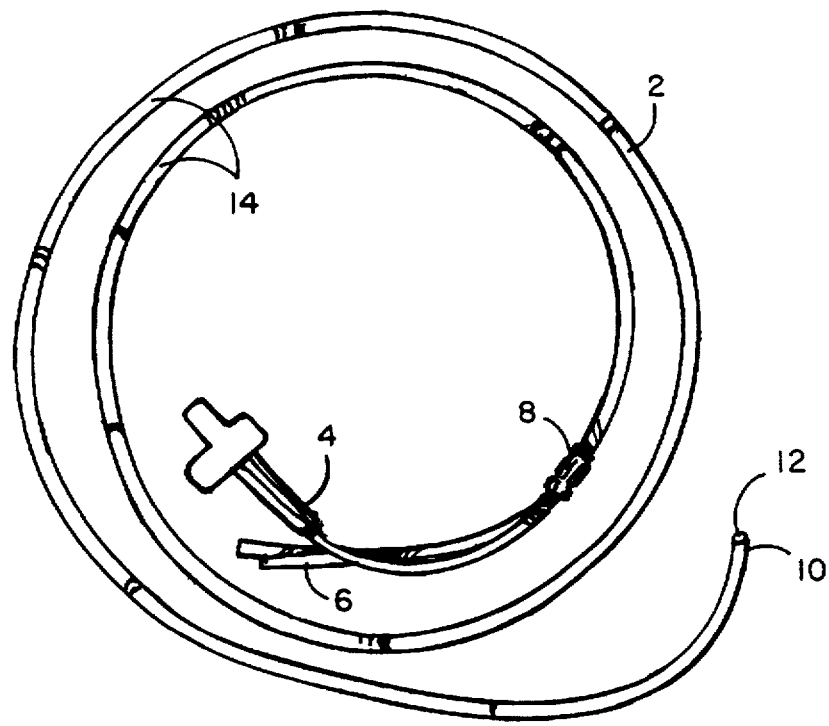
FIG. 1 is an overhead view of a conventionally known first catheter.

The present invention is a catheter apparatus and catherization technique for creating a single bypass or multiple bypasses on-demand between an unobstructed blood vessel such as the aorta and an obstructed blood vessel such as an obstructed coronary artery in-vivo. The present invention utilizes either a synthetic prosthetic tubing (or channel section) or a previously excised vascular segment as a grafted conduit; and employs an introducer system using the catheter apparatus and a graft segment in combination to create single or multiple shunts which overcome the obstruction and deliver arterial blood from a primary blood vessel, around the obstruction, into a secondary artery or vein in order to increase and/or maintain proper blood circulation in number of substantial advantages and major benefits are therefore provided by the present invention, some of which include the following:

1. The present invention provides the means for surgeons to perform multiple bypass grafts in a minimally invasive manner. The methodology permits the surgeon to utilize either synthetic prosthetic tubing (or channel sections) or previously excised veins as bypass conduits; and allows the surgeon to place each of the bypass conduits from a primary unobstructed artery (such as the aorta) to a secondary obstructed artery (such as the obstructed coronary artery) without using a heart-lung machine and without need for stopping the heart during the surgery.

2. The present invention simplifies the complexity of conventional bypass surgery and makes the surgery less invasive. Moreover, the technique provides the ability to create multiple bypass conduits using a catheterization procedure which not only shortens the conventional operation time for surgery but also makes the bypass surgery safer and more cost effective.

3. The present invention is suitable for creating a single bypass graft or multiple bypass grafts in any medical situation, condition, or pathology in which there is a need for increased blood flow to a specific blood vessel or vascular area or body region. The cause or source of the medical problem may be an obstruction in a blood vessel; or a narrowing or thickening of a blood vessel wall; or a diminution or narrowing of a vascular section in a particular blood vessel. Each of these medical conditions has its particular cause, origin, or source; and each of these pathologies, though different in origin, causes a similar effect overall—a loss of blood flow and blood pressure within the blood vessel. Accordingly, the present invention is deemed useful and desirable to overcome any of these particular medical conditions and instances where there is a demonstrated need for increased blood pressure and blood volume flow within a particular blood vessel in the body.

4. The present apparatus and methodology can be employed to create a bypass conduit between any two blood vessels. In many instances, the bypass conduit is made between a primary unobstructed artery and a secondary obstructed artery, a typical example being a bypass between the ascending aorta and an obstructed coronary artery. However, a bypass shunt may also be created between any two veins (such as between the portal vein and the inferior vena cava); or between an artery and a vein (such as between the superior vena cava and a pulmonary artery). Equally important, although the primary focus of the present invention is the thoracic cavity and the recognized need for bypass conduits among the blood vessels found therein, the present apparatus and methodology may be employed anywhere in the human body where there is a need for increased vascularization or revascularization of the local region. The sole limitation, therefore, is a means of access for the catheter apparatus, the introducer system, and the methodology to be performed by the skilled surgeon and interventional radiologist.

In order to provide a complete and comprehensive understanding of the present invention, the detailed description is given as a series of individual sections presented seriatim. These will include the following: the component parts of the catheter apparatus; the synthetic prosthetic channel section or excised blood vessel segment to be used as a bypass conduit; the introducer system utilizing the catheter apparatus and bypass conduit in combination; general techniques of catheter routing and surgical introduction; the methodology and individual manipulations for creating a bypass graft; and an illustrative summary of the preferred surgical procedures using the catheter apparatus, introducer system, and methodology. Each of these will be described and characterized individually.

The Component Parts Of The Catheter Apparatus

Three essential component parts comprise the catheter apparatus needed to create a bypass in-vivo. These are: a flexible guiding catheter; an obturator having a puncturing headpiece; and a deformable thermoelastic cuff for engaging and securing a synthetic prosthesis or a previously excised vascular segment as a bypass conduit to an unobstructed major blood vessel (such as the aorta). Each of these component parts will be described in detail individually.

A. The Flexible Guiding Catheter

The in-vivo bypass catheterization method comprising the present invention requires that a controlling or guiding flexible catheter be employed as an essential part of the apparatus and manipulations. This controlling or guiding flexible catheter has at least one tubular wall of fixed axial length; has at least one proximal end for entry; has at least one distal end for egress; and has at least one internal lumen of a volume sufficient to allow for on-demand controlled passage therethrough of a prepared obturator carrying a deformable thermoelastic cuff and a bypass conduit.

Catheters, particularly surgical catheters, are conventionally known and used; and a wide range and variety of guiding catheters are available which are extremely diverse in shape, design, and specific features. All of the essential requirements of a guiding flexible catheter exist as conventional knowledge and information in the relevant technical field; and all of the information regarding catheter design and provided in summary form hereinafter is publicly known, widely disseminated, and published in a variety of authoritative texts. The reader is therefore presumed to be both familiar with and have an in-depth knowledge and understanding of the conventional diagnostic and therapeutic uses of catheters and cathertization techniques. Merely representative of the diversity of publications publicly available are the following, each of which is expressly incorporated by reference herein: *Diagnostic and Therapeutic Cardiac Cathertization*, second edition (Pepine, Hill, and Lambert, editors) Williams & Wilkins, 1994 and the references cited therein; A Practical Guide To Cardiac Pacing, fourth edition (Moses et. al., editors) Little, Brown, and Company, 1995 and the references cited therein; *Abrams Angiography*, third edition (H. L. Abrams, editor), Little, Brown, and Company, 1983.

A number of specific types of controlling or guiding catheters are known today; but for purposes of practicing the present invention, a number of newly designed or specifically designed catheters of varying lengths and sizes suitable for bypass use are expected and intended to be developed and manufactured subsequently. Equally important, minor modifications of the presently existing general categories of catheters are equally appropriate and are expected to be found suitable for use when practicing the present invention. Accordingly, a summary review of the conventionally known catheter types as well as a overall description of general catheter design and the principles of catheter construction are presented herein.

Catheter construction and design

Presently known specific types of catheters include the following: central venous catheters which are relatively short (usually 20–60 centimeters) in length and are designed for insertion into the internal jugular or subclavian vein; right heart catheters such as the Cournard catheter designed specifically for right heart catheterization; transseptal catheters developed specifically for crossing from right to left atrium through the interarterial septum at the fossa ovalis; angiographic catheters which are varied in shape and are frequently used today in the femorial and brachial approach for cardiac catheterization and angiography in any of the major vessels; coronary angiographic catheters which include the different series of grouping including Sones, Judkins, Amplatz, multipurpose, and bypass graft catheters; as well as many others developed for specific purposes and medical conditions.

Figure 2:
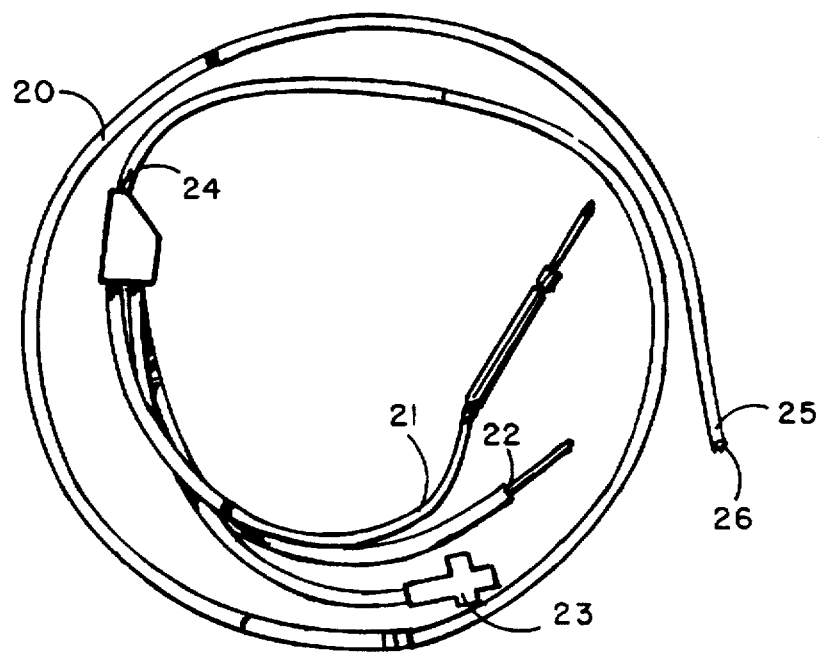
FIG. 2 is an overhead view of a conventionally known second catheter.

Merely representative of guiding and controlling flexible catheters, generally presented herein without regard to their specific past usages or intended applications, are those illustrated by FIGS. 1 and 2 respectively. As exemplified by FIG. 1, a catheter 2 is seen having a tubular wall of fixed axial length; having two proximal portals 4 and 6 which together generate the proximal end 8 for entry into the interior of the catheter; a single distal portal 10 and the distal end 12 of the catheter; and an internal lumen 14 (which is not visible in the illustration).

Another variation commonly known is illustrated by FIG. 2 which shows a controlling flexible catheter 20 having a tubular wall of fixed axial length; three proximal portals 21, 22 and 23 respectively which collectively form the proximal end 24 for entry into the internal volume of the catheter; and a single distal portal 25 which designates the distal end 26 or tip of the catheter. It will be appreciated and understood that FIGS. I and 2 are presented merely to show the overall general construction and relationship of parts present in each flexible controlling catheter suitable for use with the present methodology.

In accordance with established principles of conventional catheter construction, the axial length of the catheter may be composed of one or several layers in combination. In most multilayered constructions, one hollow tube is stretched over another to form a bond; and the components of the individual layers determine the overall characteristics for the catheter as a unitary construction. Most multilayered catheters comprise an inner tube of teflon, over which is another layer of nylon, woven Dacron, or stainless steel braiding. A tube of polyethylene or polyurethane is then heated and extruded over the two inner layers to form a bond as the third external layer. Other catheter constructions may consist of a polyurethane inner core, covered by a layer of stainless steel braiding, and a third external jacket layer formed of polyurethane.

Several examples of basic catheter construction and design are illustrated by FIGS. 3–6 respectively. FIGS. 3A and 3B are perspective and cross-sectional views of a single tubular wall considered the standard minimum construction for a catheter. FIGS. 4A and 4B are perspective and cross-sectional views of a thin-walled design for a single layer extruded catheter. In comparison, FIGS. 5A and 5B are perspective and cross-sectional views of a standard multi-layered catheter construction having a braided stainless steel midlayer in its construction. Finally, FIGS. 6A and 6B are perspective and cross-sectional views of a thin-walled design for a multilayered catheter with a braided stainless steel middle layer.

Catheters are generally sized by external and internal diameter and length. The internal specified either by diameter (in thousandths of an inch or millimeters or French). Many newer thin-walled catheter designs provide a much larger internal lumen volume to external diameter ratio than has been previously achieved; and this has resulted in catheters which can accommodate much more volume and allow the passage of much larger sized articles through the internal lumen. External diameter is typically expressed in French sizes which are obtained by multiplying the actual diameter of the catheter in millimeters by a factor of 3.0. Conversely, by traditional habit, the size of any catheter in millimeters may be calculated by dividing its French size by a factor of 3.0. French sizes from 5–8 are currently used for diagnostic angiography. For purposes of practicing the present invention, it is also desirable that French sizes ranging from 4–16 respectively be employed unless other specific size requirements are indicated by the particular application or circumstances. In addition, because of the variation between standard, thin-walled, and super high-flow catheter construction designs, a range and variety of external and internal lumen diameter sizes exist. To demonstrate the conventional practice, the data of Table 1 is provided.

56 and 58 respectively. Thus, in this alternative construction, the discrete volume of internal lumen 56 is markedly smaller than the volume of the adjacently positioned internal lumen 58; and yet both of these internal lumens 56 and 58 exist in, are adjacently positioned, and are both contained within a commonly-shared single tubular wall.

Figure 7A:
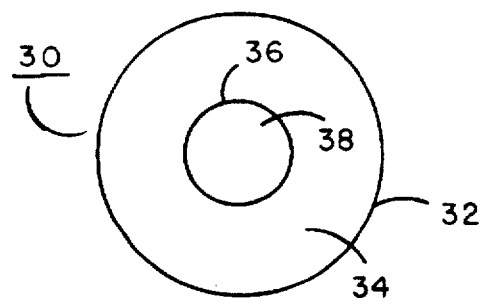
FIGS. 7A–7D are cross-sectional views of four different constructions of dual-lumen catheters.
Figure 7B:
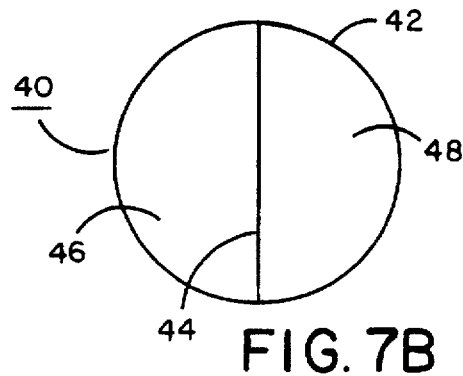
Figure 7C:
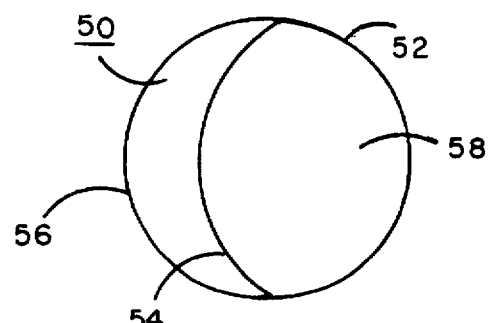
Figure 7D:
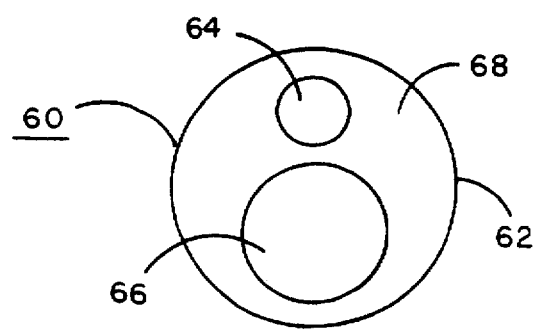

A fourth construction and design for a dual-lumen catheter is presented by FIG. 7D which shows a catheter 60 having a single external tubular wall 62 of relatively large size and thickness. Within the material substance 68 of the tubular wall 60 are two discrete bore holes 64 and 66 of differing diameters which serve as two internal lumens of unequal volume. Internal lumen 64 is clearly the smaller while internal lumen 66 is far greater in spatial volume. Yet each internal lumen volume 64 and 66 is adjacent to the other, lies in parallel, and follows the other over the axial length of the catheter.

In general, the tubular body of the catheter is generally straight over most of its length and may have different bends

TABLE 1

External and Lumen Diameter Measurements in Standard, Thin-Walled, and Super High-Flow Diagnostic Catheters

| French | External Diameter | | Standard (High Torque) | | Internal Diameter | | | |
|---|---|---|---|---|---|---|---|---|
| | | | | | Thin-Walled (High Flow) | | Super (High Flow) | |
| Size | inches | mm | inches | mm | inches | mm | inches | mm |
| 5 | 0.065 | 1.67 | * | * | 0.044 | 1.08 | 0.052 | 1.28 |
| 6 | 0.078 | 2.00 | * | * | 0.050 | 1.27 | 0.056 | 1.42 |
| 7 | 0.092 | 2.34 | 0.048 | 1.22 | 0.056 | 1.42 | 0.061 | 1.55 |
| 8 | 0.104 | 2.64 | 0.056 | 1.42 | 0.063 | 1.60 | * | * |
| 9 | 0.118 | 3.00 | * | * | * | * | * | * |

*No catheters made in this size/type.

Dual-lumen catheters

A number of different dual-lumen catheters are known today which differ in the size and spatial relationship between their individual lumens. This is illustrated by FIGS. 7A–7D respectively which show different dual-lumen constructions for four catheters having similar or identical overall diameter (French) size.

As shown therein, FIG. 7A shows a dual-lumen catheter 30 wherein a first external tubular wall 32 provides an outer lumen volume 34 into which a second internal tubular wall 36 has been co-axially positioned to provide an inner lumen volume 38. Clearly, the construction of catheter 30 is a co-axial design of multiple tubular walls spaced apart and co-axially spaced but separate internal lumens of differing individual volumes.

In comparison, FIG. 7B shows a second kind of construction and design by dual-lumen catheter 40 having a single external tubular wall 42; and an centrally disposed inner septum 44 which divides the interior tubular space into two approximately equally lumen volumes 46 and 48 respectively. Thus, in this construction, the diameter, length, and volume of internal lumen 46 is effectively identical to the diameter, length and volume of internal lumen 40; and both of these exist and are contained within a single, commonly-shared, tubular wall.

Figure 8:
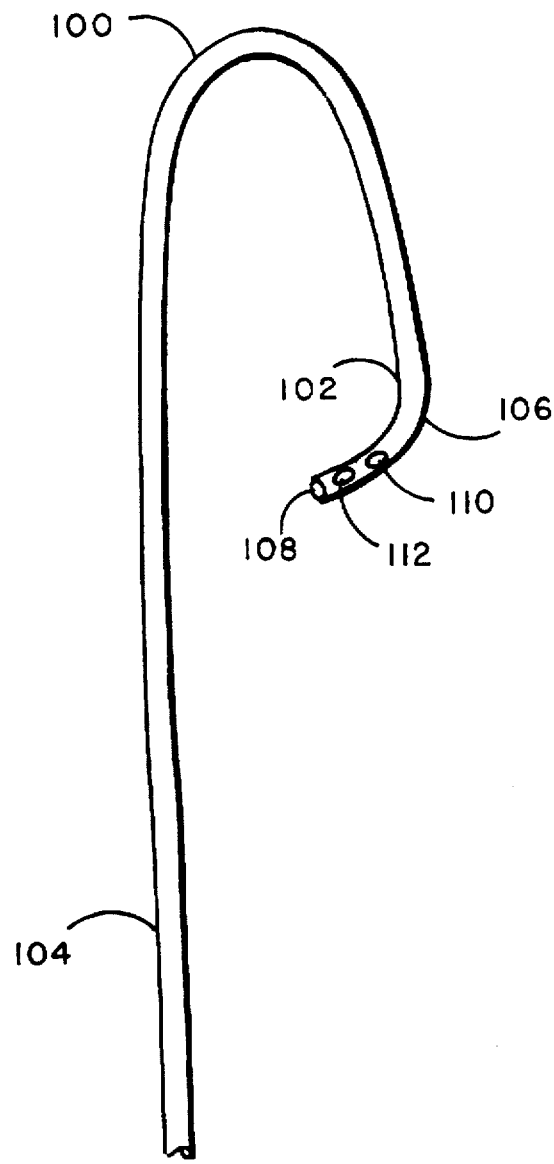
FIG. 8 is an illustration of the distal end of a conventionally known guiding catheter.

A third kind of construction is illustrated by FIG. 7C and shows an alternative kind of construction and design to FIG. 15B. As seen in FIG. 7C, dual-lumen catheter 50 has a single external tubular wall 52; and contains an asymmetrically positioned internal divider 54 which divides the interior tubular space into two unequal and different lumen volumes or curves towards the distal end or tip. A representative illustration of the distal end of a catheter is illustrated by FIG. 8. The individual bends in the catheter are traditionally called "curves"; and the terms "primary, secondary, etc.," are applied to each additional curve further away from the distal tip as is illustrated by FIG. 8. Accordingly, the primary curve 100 is followed by the secondary curve 102 for the catheter body 104 generally. The catheter tip 106 is its most distal segment. In addition, the catheter distal tip 106 may have any combination of a single end hole 110 or an open distal end 108 and any number of side holes 110, 112 which function as portals for fluids and gases exiting the distal end of the catheter.

Conventional practice permits a number of different distal ends or tips which vary in design and appearance. Merely representative of these permitted and conventional variances in distal end design for catheters generally are the distal ends of ventricular catheters which include: a "pigtail" design and construction which has a curled-tip format and multiple side holes; the Lehman ventricular catheter end which provides a number of side holes in different places along the distal end; and the Gensini design which provides multiple side holes at varying angles. Accordingly, for purposes of practicing the present repair methodology, any construction of the catheter distal end whether having one or more curves, or none; and whether or not there is more than one central portal for exiting the lumen or multiple side holes, are all considered conventional variations in construction design. Any and all of these distal tip designs and constructions are therefore deemed to be encompassed completely and to lie within the general catheter scope of construction suitable for use with the present invention.

B. The Obturator

The second requisite component part of the catheter apparatus is the obturator. Each embodiment of an obturator is comprised of at least three parts, and preferably comprises four component parts. The minimal requisite three elements include a puncturing headpiece; a perforating end tip on the headpiece; an elongated shaft integral with the puncturing headpiece. The fourth highly desirable component is the means for expanding and contracting the size of the puncturing headpiece on-demand. Various embodiments representative of each of these structural components are individually illustrated within FIGS. 9–15 respectively.

One general embodiment of an obturator is illustrated by FIGS. 9–10. As seen therein, the obturator 120 comprises a puncturing headpiece 122 which is substantially bullet-shaped (frusto-conical) in configuration, and comprises an outer shell 124 and a base plate 126. The outer shell 124 has determinable surface dimensions and an overall girth which can be either fixed or varied in size. At the distal end 128 of the puncturing headpiece 122 is a perforating end tip 130 which appears as a cross-shaped (or cone-shaped) cutting edge for the headpiece 122. As shown by FIG. 10, the perforating end tip 130 does not extend over the entire surface area of the outer shell 124; instead, the perforating end tip 130 is limited in size and orientation to the distal end 128. The perforating end tip 130 serves as the sharp cutting edge for the obturator 120 as a whole.

Integral with the puncturing headpiece 122 is an elongated shaft 134 whose overall axial length may be varied to accommodate the surgeon and the particular medical circumstances of usage. The distal end 136 of the shaft is integrated with the puncturing headpiece 122 and can provide access to the interior volume of the headpiece bounded by the outer shell 124 and the base plate 126. The proximal end 138 of the elongated shaft 134 is intended to be held by the surgeon performing the vascular bypass surgery. Accordingly, the axial length of the elongated shaft 134 will vary and accommodate the surgeon; and thus vary from a few inches to a few feet in length. The function of the elongated shaft 134 is for the carrying and transport of a bypass conduit to the chosen site on the unobstructed or primary blood vessel in-vivo. The elongated shaft 134 acts to support, maintain and convey the conduit within the lumen of the catheter in a manner such that the conduit can be used as a bypass graft.

The fixed size embodiments of the obturator

The minimalist format for the obturator does not provide any means nor mechanism to alter the surface dimensions or configuration of the puncturing headpiece integrated with the elongated shaft. Thus, the initial dimensions and girth for the puncturing headpiece 122 shown by FIGS. 9 and 10 respectively will remain constant and fixed; and neither the size, shape, aspect ratios, nor overall geometry will be changed or modified during the intended in-vivo use for the obturator embodiment. The fixed size embodiment, however, is a less preferred format for clinical applications; and this minimalist format may cause more procedural difficulty and inconvenience for the surgeon than the preferred variable-size embodiments of the obturator.

The variable-size embodiments of the obturator

A highly desirable and preferred component feature of the puncturing headpiece and the obturator as a whole is that means exist for expanding and contracting the puncturing headpiece on-demand. The effect of this fourth feature and capability for the obturator is illustrated by FIGS. 11–13 respectively. As seen within FIG. 11, the puncturing headpiece 122 appears in its initial size identical to that shown by FIGS. 9 and 10. The outer shell 124 is substantially cone-shaped in configuration, has an initial internal volume, and has a girth dimension d equal to the initial diameter of the base plate 126. The internal volume of the puncturing headpiece, as determined by the dimensions of the outer shell 124 and the base plate 126, provides an initial internal volume of determinable quantity.

When the mechanism for contracting the puncturing headpiece is activated, the consequence is illustrated by FIG. 12 in which the dimensions of the outer shell 124 have been diminished and the girth of the headpiece has been reduced as shown by the reduced diameter d' of the base plate 126. Note also, that as the puncturing headpiece 122 becomes contracted in overall volume and dimensions, the configuration of the puncturing headpiece 122 has consequentially become altered and now appears to be spear-like in configuration. Similarly, the overall angular disposition of the perforating end tip 130 serving as the cutting edge will also be slightly altered in overall appearance as a consequence of contracting the puncturing headpiece 122.

Alternatively, when the puncturing headpiece 122 is expanded, the overall result is shown by FIG. 13. As seen therein, the outer shell 124 has been expanded in overall dimensions and volume; and the girth of the headpiece has been expanded and can be determined by the diameter d" of the expanded base plate 126. Note that the overall appearance of the puncturing headpiece has been altered as a consequence of its expansion and now appears to be elliptical in shape overall. Similarly, the perforating end tip 130 has similarly been altered in appearance and has angularly expanded somewhat to conform with the expanded dimensions and angularity of the outer shell 124.

It will be recognized and appreciated also that throughout the changes in appearance, internal volume (designated as V, V' and V") and overall size for the contracted or expanded puncturing headpiece 122 (as shown via FIGS. 11, 12, and 13 respectively), the dimensions and overall configuration of the elongated shaft 134 have not been altered meaningfully or significantly. Although this is not an absolute requirement in each and every embodiment of an obturator, it is preferred that the elongated shaft 134, particularly at the integrated distal end 136, remain constant in size and volume as much as possible and be unaffected subsequent to the on-demand expansion or contraction of the puncturing headpiece 122. This preference and feature will maintain the integrity of the synthetic prosthesis or the excised vascular segment intended to be carried and transported by the elongated shaft during the bypass grafting procedure. Thus, to avoid or minimize any physical damage to the graft material, it is desirable that the elongated shaft be maintained in appearance, configuration and dimensions without change whenever possible.

Means for contracting or expanding the puncturing headpiece

A feature and component of each preferred obturator is the existence and availability of specific means for expanding and contracting the puncturing headpiece on-demand. A number of different mechanisms and means for expanding and contracting the puncturing headpiece of the obturator are conventionally known and easily employed. Merely to demonstrate some different and conventionally known mechanisms, attention is directed to the means illustrated by FIGS. 14 and 15 respectively.

The means for expanding and contracting the puncturing headpiece on-demand illustrated by FIG. 14 constitute a mechanical approach and design mechanism which is carried within the internal volume of the puncturing headpiece 122 and the integrated elongated shaft 134. As seen therein, a central rod 150 extends through the hollow interior of the elongated shaft 134 and extends into the internal volume defined by the outer shell 124 and the base plate 126 of the puncturing headpiece 122. Within the internal volume of the outer shell 124, a plurality of rotable ribs 152 are joined to the central rod 150 at the distal end to form a central pivot point 154. Each rotable rib 152 is mobile and pivotable around the central point 154 and forms an umbrella-like scaffolding structure which can be expanded outwardly or collapsed inwardly at will. Mounted on the central rod 150 is an expansion wheel 156. This expansion wheel 156 is centrally mounted on the rod 150; is moveable over the axial length of the central rod 150; and is controlled in the direction of axial movement (distally and proximally). The expansion wheel 156 comprises a center hub 158 and a plurality of hub supports 160, both of which maintain the expansion wheel in proper position as it engages the plurality of rotable ribs 152. Joined to the central hub 158 of the expansion wheel 156 are linear movement members 162 which are positioned within the interior volume of the elongated shaft 134 and have a length sufficient to reach to the proximal end 138 of the elongated shaft 134 for control by the surgeon or invasive radiologist. The linear movement members 162 engage the center hub 158 of the expansion wheel 156; and extend or withdraw the expansion wheel closer to or away from the perforating end tip 130 of the puncturing headpiece 122. When the expansion wheel is engaged and pushed forward, expansion wheel engages the rotable ribs 152 and expands the rotable ribs outwardly thereby increasing the overall girth of the puncturing headpiece as a unit. Alternatively, when the linear movement members 162 are withdrawn, the expansion wheel recedes towards the proximal end and the engaged rotable ribs 152 collapse inwardly within the volume of the outer shell 124. The consequence of this movement is a contraction of the puncturing headpiece 122 as a unit. It will be recognized and appreciated that this mechanical approach for expanding and contracting the puncturing headpiece is completely conventional in design and operation; and accordingly, any conventional refinement of these basic component parts is considered to be a variation within the scope of this mechanical system.

Figure 15:
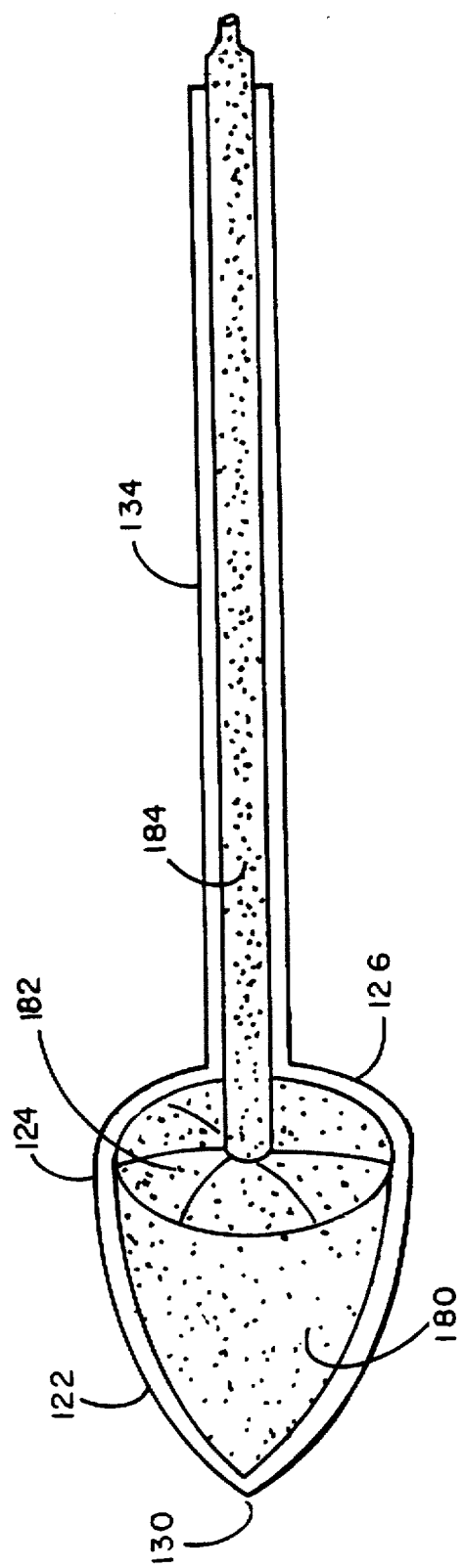
FIG. 15 is an exposed view of a hydraulic assembly for expanding and contracting a puncturing headpiece on-demand in an obturator.

As a representated alternative, hydraulic means for expanding and contracting the puncturing headpiece of the obturator on demand is also provided. In this system, as shown by FIG. 15, the internal volume of the puncturing headpiece 122 and the integrated elongated shaft 134 includes an elastic sack 180 comprised of a fluid containing elastic bubble 182 and a fluid delivering elastic conduit 184. The outer shell 124 and base plate 126 of the puncturing headpiece 122 are as previously shown; and the headpiece 122 is integrated with the elongated shaft 134 as previously described herein. Within the internal volume of the puncturing headpiece 122, is a fluid containing elastic bubble 182 which is in fluid communication with the elastic conduit 184 carried within the internal volume of the elongated shaft 134. The elastic sack 180 is formed of elastomeric material (such as rubber, elastic plastic, and the like) and is fluid-tight along its seams. The elastic sack 180 contains any liquid which is compatible with the material of the elastic sack; and it is the intrinsic nature of the material forming the elastic sack 180 that the material exerts a compression force or pressure upon the fluid contained within the elastic sack itself. In this way a hydraulic system for expanding and contracting the puncturing headpiece of the obturator is created.

As fluid is introduced through the elastic conduit 180 by the surgeon or invasive radiologist, that fluid is conveyed and delivered into the elastic bubble 182 positioned within the puncturing headpiece 122. The elasticity of the bubble 182 exerts a mild compression force and pressure against the quantity of fluid contained within the bubble interior volume; accordingly, the greater the quantity of fluid within the elastic bubble 182, the larger in overall volume the elastic bubble becomes. Thus, as more fluid is delivered through the conduit 184 into the elastic bubble 182, the larger in overall volume the elastic bubble becomes; and as the volume of the elastic bubble expands, the overall configuration and internal volume of the piercing headpiece 122 also enlarges. In this manner, by carefully controlling the amount of fluid conveyed through the conduit 184 into the elastic bubble, the overall size and configuration of the piercing headpiece 122 can be controllably expanded. Subsequently, to reduce the overall size and configuration of the puncturing headpiece 122, a quantity of fluid is permitted to be released from the elastic conduit 184 at the proximal end by the surgeon or radiologist. Because the material is elastic and exerts a compression force against the quantity of fluid present within the bubble at any given moment in time, the release of fluid through the elastic conduit will cause a reduction in overall size for the elastic bubble 182; and as the overall volume of the elastic bubble is reduced in size, the puncturing headpiece will consequently be contracted and reduced in configuration and overall volume as well. It will be noted and appreciated also that this hydraulic mechanism for expanding and contracting the puncturing headpiece on demand is a conventionally known fluid system and technique; and many conventionally known variations and changes in hydraulic design and fluid control systems are presently known and commonly available for use. Accordingly, all hydraulic systems are envisioned as suitable for use as one means for expanding and contracting the puncturing headpiece of the obturator on-demand.

Alternative obturator structures

A number of different physical embodiments for the obturator are also envisioned and intended for use. Some examples, which are merely illustrative of the range and variety of physical formats and which serve to merely illustrate the range and degree of difference available for the various puncturing headpieces of an obturator, are illustrated by FIGS. 16–22 respectively. It will be recognized and understood, however, that these alternative embodiments are merely representative of obturators and puncturing headpieces generally and do not signify any limitation or restriction on their structural construction or design.

The embodiment illustrated by FIGS. 16 and 17 respectively shows a puncturing headpiece 200 which is substantially cone-shaped in overall appearance and comprises an outer shell 202 and a base plate 206. The distal end 208 of the puncturing headpiece 200 has a perforating end tip 210 which is also substantially cone-shaped in configuration and appearance and covers only a small surface area of the outer shell 202. Integral with the puncturing headpiece is the elongated shaft 134 as described previously herein; and means for expanding and contracting the puncturing headpiece 200 on-demand are included within the obturator as a integrated unit.

Another embodiment for the puncturing headpiece is illustrated by FIGS. 18 and 19 respectively. As shown therein, the puncturing headpiece 220 comprises the outer shell 222 and the base plate 224 integral with the elongated shaft 134. A particular feature of this embodiment, however, is the distal end 226 seen most clearly within FIG. 19 as providing a perforating end tip 230 which is substantially star-shaped and extends over the surface area of the outer shell 222. The result is to provide a series of grooves 228 alternating with sharp cutting edges 232 over the surface of the outer shell 222. This embodiment for the puncturing headpiece 220 provides a much greater area for cutting and perforation as a specific feature of the obturator design.

To demonstrate further the variety and degree of differences envisioned and intended when constructing a puncturing headpiece, the structural constructions exemplified by FIGS. 20–22 respectively are provided. As illustrated by FIG. 20, the puncturing headpiece 250 includes a buttressing region 254 as a part of the outer shell 252. The buttressing region 254 is a reinforced region for engaging materials placed in contact with the outer shell when the puncturing headpiece is expanded. The puncturing headpiece 250 includes a base plate 256 and is integrated with the elongated s haft 134 (describe d previously herein).

In comparison, the puncturing headpiece 260 exemplified by FIG. 21 is a sharply tapered and contoured embodiment in which the outer shell 262 includes a spiral girth zone 264 suitable for deforming elastic materials. The base plate 266 conforms to and is integrated with the spiral zone 264.

Another alternative embodiment of the puncturing headpiece is illustrated by FIG. 22. In this embodiment, the puncturing headpiece 280 comprises an outer shell 282 and a concave-shaped or scalloped zone 284 which is joined to and integrated with the base plate 286. The concave-shaped configuration of the zone 284 is intended to aid the puncturing headpiece as it is expanded and contracted on-demand.

C. The Deformable Thermoelastic Cuff

An essential component part of the catheter apparatus and method for creating a bypass graft is the presence and use of a deformable thermoelastic cuff comprised of a shape-memory alloy composition.

The shape-memory metal alloy compositions to be used with the present invention constitute conventionally known blends and formulated metallic mixtures of nickel and titanium which undergo a phase transition—that is, a molecular rearrangement of atoms, molecules or ions within a lattice structure—due to a temperature change. The unique capability of shape-memory alloys is that these alloys change shape or configuration as a direct consequence of a change in temperature; and the alloy composition "remembers" its earlier and specifically prepared shape because the phase change affects its structure on the atomic level only, without disturbing the arrangement of the molecules which would otherwise be irreversible.

When these shape-memory alloys are intentionally superheated far above their transition temperature (either electrically or by external heat), a stretched temperature transformed alloy format results which contracts and exerts considerable force; and the temperature transformed alloy composition will become memory-shaped in a fixed specific configuration. Afterwards, when cooled to below its transition temperature, the alloy composition can then be bent and shaped into other configurations while retaining the fixed "memory" of the particular shape in the earlier superheated condition. Thus, these shape-memory alloy compositions are recognized as being both deformable and thermoelastic, as well as being able to revert to a prepared memory-shaped configuration as a consequence of being warmed to a temperature above its individual transition temperature.

Alloy formulations

At least twenty different formulations of these alloys are conventionally known to exhibit the shape-memory effect and property, all of these comprising different mixtures of nickel and titanium in varying percentage ratios [*Design News*, Jun.21, 1993 issue, pages 73–76]. These metal alloys are today utilized in the manufacture of differing products. For example, a range of different shape-memory alloy wires are commercially available in diameters from 0.001–0.010 inches [Dynalloy Inc., Irvine, Calif]. In addition, surgical anchors having superelastic properties and formed by two or more arcs of wire strands (which can withstand strains exceeding 10%) have been developed [Mitek Surgical Products, Inc., Norwood, Mass.]. Also, blood clot filters formed of shape-memory alloy wires are commercially sold for implantation in large blood vessels such as the vena cava [Nitinol Medical Technologies, Inc., Boston, Mass.]. While these commercially available products illustrate the use of one or more shape-memory alloy formulations by the manufacture of their particular articles, a more general listing of conventionally known properties and characteristics for shape-memory alloy compositions is provided by Table 2 below.

TABLE 2

Conventionally Known Properties Of Shape-Memory Alloys[1]

| Transformation Properties | |
|---|---|
| Transformation Temperature | −200 to 110° C. |
| Latent Heat Of Transformation | 5.78 cal/g |
| Transformation Strain (for polycrystaline material) | |
| for a single cycle | 8% maximum |
| for $10^2$ cycles | 6% |
| for $10^5$ cycles | 4% |
| Hysteresis* | 30 to 50° C. |
| Physical Properties | |
| Melting point | 1300° C. (2370° F.) |
| Density | 6.45 g/cm$^3$ (0.0233 lb/in$^3$) |
| Thermal Conductivity | |
| austenite | 0.18 W/cm · °C. (10.4 BTU/ft · hr · °F.) |
| martensite | 0.086 W/cm · °C. (5.0 BTU/ft. · °F.) |
| Coefficient of Thermal Expansion | |
| austenite | 11.9 × 10$^{-6}$/°C. (6.11 × 10$^{-6}$/°F.) |
| martensite | 6.6 × 10$^{-6}$/°C. (3.67 × 10$^{-6}$/°F.) |
| Specific Heat | 0.20 cal/g · °C. (0.20 BTU/lb · °F.) |
| Corrosion Performance** | excellent |
| Electrical Properties | |
| Resistivity (ρ) [resistance = ρ · length/cross-sectional area] | |
| austenite | ~100 μΩ · cm (~39.3 μΩ · in) |
| martensite | ~80 μΩ · cm (~31.5 μΩ · in) |
| Magnetic Permeability | <1.002 |
| Magnetic Susceptibility | 3.0 × 10$^6$ emu/g |
| Mechanical Properties | |
| Young's Modulus*** | |
| austenite | ~83 GPa (~12 × 10$^6$ psi) |
| martensite | ~28 to 41 GPa (~4 × 10$^6$ to 6 × 10$^6$ psi) |
| Yield Strength | |
| austenite | 195 to 690 MPa (28 to 100 ksi) |
| martensite | 70 to 140 MPa (10 to 20 ksi) |
| Ultimate Tensile Strength | |
| fully annealed | 895 MPa (130 ksi) |
| work hardened | 1900 MPa (275 ksi) |

TABLE 2-continued

Conventionally Known Properties Of Shape-Memory Alloys[1]

| | |
|---|---|
| Poisson's Ratio | 0.33 |
| Elongation at Failure | |
| fully annealed | 25 to 50% |
| work hardened | 5 to 10% |
| Hot Workability | quite good |
| Cold Workability | difficult due to rapid work hardening |
| Machinability | difficult, abrasive techniques are preferred |

*Values listed are for a full martensite to austenite transition Hysteresis can be significantly reduced by partial transformation or ternary alloys
**Similar to 300 series stainless steel or titanium.
***Highly nonlinear with temperature.
[1]Design News, June 21, 1993 issue, p. 77.

All the different specific formulations and metallic blends comprising nickel and titanium which yield a deformable, thermoelastic, shape-memory alloy composition are suitable for use when practicing the present methodology. All of these shape-memory alloys rely on a crystal phase change from a higher temperature Austernite form to a lower temperature Martensite form to accomplish the memory effect. The cubic Austernite phase behaves much like ordinary metals as it deforms. In contrast, the complex crystal Martensite form can be found by reversible movement of twin boundaries to change the average "tilt" or strain in each segment of the alloy. The overall strain can be eliminated by releasing the stress, by maintaining it if it is not thermally stable (the superelastic effect), or by healing the alloy to change it back to Austenite form (shape-memory effect).

The crystal transformation of shape-memory alloy compositions is, by definition, thermoelastic—i.e., it progresses in one direction on cooling below the transition temperature and in the other direction upon heating above the transition temperature. The amount of transformation change versus temperature, measured either as the percent of Martensite form or the strain in a constantly stressed element, is a function of and can be plotted against temperature (°C.) directly; and the change from one phase (and identifiable shape) to another typically occurs in a narrow temperature range (often 5°–10° C.). Hysteresis takes place before the reverse transformation occurs.

The amount of strain accommodated due to the movement of twin boundaries, differs in each metallic alloy blending system. In the nickel-titanium system for example, up to 8% reversible tensile strain is available; however, to guarantee a long life use, the strain is often limited to 4–5%.

The stress-strain behavior of shape-memory alloy compositions is employed to help explain the shape-memory effect. For instance, Martensite is much easier to deform than Austenite. Therefore, one can deform the alloy while cold with much less force than when heated to change it back into Austenite form. As a result, the alloy converts thermal energy to mechanical work at high forces.

Fixing the memory-shaped configuration in the metal alloy

To prepare and fix the particular (or desired) shape to be "remembered" when the alloy undergoes a temperature phase transition, the alloy composition must be superheated initially to about 500° C. (or roughly 930° F.) for an hour while held in the fixed shape and position to be memorized. During the superheating process, the native alloy blend enters what is called the Austenite phase—a rigid lattice of nickel atoms surrounded by titanium alloys. Then, as the alloy metal cools below its transition temperature (which will vary with the percentage proportions of nickel and titanium), the alloy composition adopts the Martensite phase, in which the nickel and titanium atoms assume a very different arrangement—one that is very easy to bend and deform. Subsequently, when the deformed metallic alloy is reheated to the chosen transition temperature range between 25°–35° C., thermal motion causes the atoms to snap back into the Austerine phase, thereby restoring the fixed memory-shaped configuration of the object [Invention & Technology, Fall 1993, pages 18–23 ].

For purposes of practicing the present in-vivo repair methodology, it is most desirable that the shape-memory alloy composition be prepared in a metallic blend and formulation such that the temperature transition phase occurs at a temperature less than about 35° C.; but greater than about 25° C.; and preferably be in the range from about 30°–35° C. This preferred 30°–35° C. transition phase temperature range is dictated by the demands of the human body which maintains a normal temperature at about 37° C. (98.6° F.); and typically shows a normal temperature range and variance of one or two degrees Celsius above and/or below this normative temperature standard. It is for this reason that the broad temperature range be about 25°–35° C. and the preferred temperature transition occur in the range of 30°–35° C.; but that such transformation into the intended and fixed memory-shaped configuration occur at least by a temperature of 35° C. to insure a safety margin of medical usefulness.

The shaped configurations of the alloy cuff at temperatures less than 25°–35° C. and at temperatures greater than 25°–35° C.

The shaped cuff configurations of the thermoelastic alloy composition at temperatures less than about 25°–35° C. (a temperature below its transition temperature at which the alloy exists in the Martensite phase) may take a broad variety of different lengths, diverse dimensions, and disparate overall configuration. Merely exemplifying the range and diversity of three-dimensional forms into which the thermoelastic alloy compositions can be shaped into a cuff or flange structure at temperatures below 25° C. are those illustrated by FIGS. 23–26 respectively. For purposes of practicing the present invention, FIGS. 23 and 24 are considered more preferred embodiments and constructions of the cuff-shaped alloy structures, while FIGS. 25–26 respectively represent formats and fabrications of the deformed alloy compositions in less frequently utilized cuff-shaped configurations.

Figure 23B:
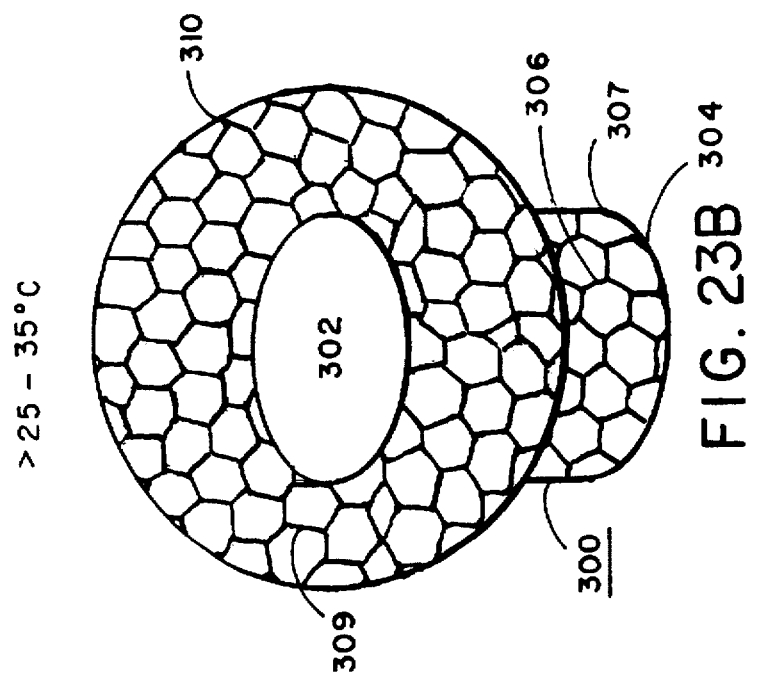
FIGS. 23A and 23B are views of a preferred first deformable cuff in the original undeformed state and the thermally deformed state.
Figure 23A:
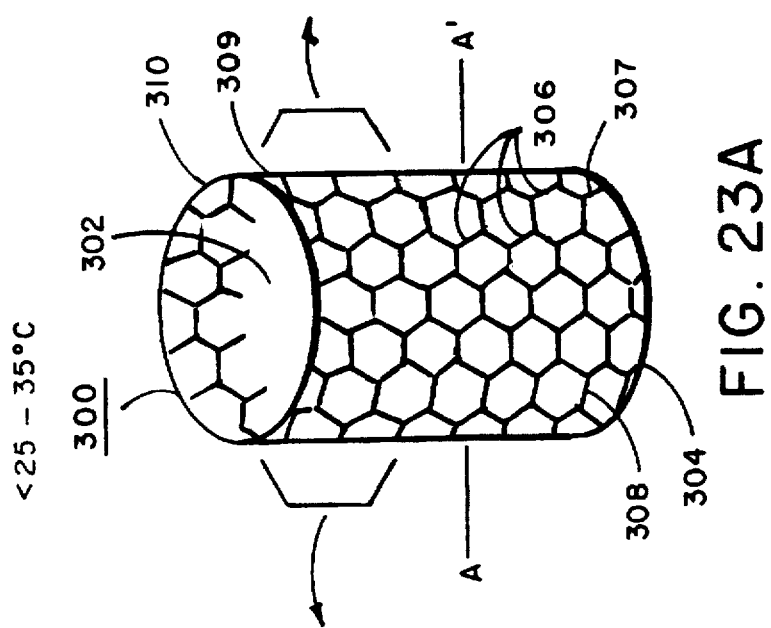

As illustrated and embodied by FIGS. 23A and 23B, the deformable thermoelastic cuff 300 is a substantially cylindrical-shaped collar which is open at each of its ends 302, 304. The cuff 300 is hollow; is substantially round or oval (in cross-sectional view); and has a determinable first configuration and dimensions initially which are deformed at will into a second memory-shaped configuration when placed at a temperature greater than about 25-35° C.

It is most desirable that the thermoelastic material constituting the sidewall 306 of the cuff 300 be prepared and initially-shaped as a first-configuration along the axis AA' as shown within FIG. 23A; and that the thermoelastic material constituting the sidewall 306 be an open-weave pattern of a memory-shaped alloy rather than take form as a solid mass of thermoelastic alloyed material. For this reason, the sidewall 306 illustrated within FIG. 23A appears in the first configuration as an open meshwork of wires 308 which are intertwined to form a substantially hexagonal pattern. This open meshwork of wires 308 provides the desired resiliency, flexibility, and memory-shaped deformation capability (particularly along the axis AA') such that the upper portion of the sidewall 306 will become deformed and flaired outwardly on-demand to yield the memory-shaped second configuration constituting the flaired-lip deformity 310 shown by FIG. 23B.

It will be recognized and appreciated that the deformed cuff shown by FIG. 23B is merely the result of removing the cuff structure from a temperature less than 25°–35° C. and placing it into a temperature environment greater than about 35°–35° C. Thus, solely as a consequence of the change in temperature, the uppermost portion 309 of the open meshwork of wires 308 above the axis AA' has become deformed such that the upper sidewall 309 adjacent to the open end 302 has expanded outwardly, flaired, and become bent into a curved lip configuration in the memory-shaped deformed state. Note that in FIG. 23B the open meshwork of wires constituting the lower portion 307 of the sidewall 306 at the other open end 304 remains relatively stable and substantially unaltered in its original shape and state; alternatively, however, the lower sidewall portion 307 can be made to expand outwardly so that it will fit more tightly within the perforation in the vascular wall. The deformation thus is controlled and the forces preferably applied to the upper sidewall portion from the AA' axis to cause the outwardly extending, flaired lip result. Moreover, the resulting flaired lip zone 310 retains structural strength and resiliency as an open meshwork of wires despite having been created by deformation. The ability of the cuff to be deformed in the manner illustrated by FIGS. 23A and 23B respectively is a requisite and necessary attribute and characteristic of each embodiment and construction for the deformable thermoelastic cuff.

The construction and design for the thermoelastic cuff in the present invention is an example of the engineering principle that structural form follows intended function. As a requisite component part of the catheter apparatus and methodology for creating a bypass conduit in-vivo, the intended functions of the thermoelastic cuff are twofold in nature: (1) the temperature-deformable cuff is intended to engage and become joined to either a synthetic prosthesis or a previously excised vascular segment which will serve as the bypass graft in-vivo; and (2) the temperature-deformable cuff is intended to be positioned within the internal lumen of an unobstructed major blood vessel (such as the aorta) and become thermally deformed in-situ such that a portion of the cuff wall becomes positioned and secured to the internal lumen (the blood flow channel) of the unobstructed blood vessel permanently and in a fluid-tight manner. Thus, as illustrated by the embodiment of FIGS. 23A and 23B, the uppermost region 309 of the alloy comprising the cuff 300 is deformed on-demand by warming to a temperature greater than 25°–35° C. and deforms into a flaired outwardly bent form which is intended to be secured within the lumen of the unobstructed artery or vein. The undisturbed sidewall portion 307 of the cuff is retained in unaltered form for engagement and juncture to the conduit segment which will serve as the bypass graft.

Several attributes and characteristics are commonly to be shared among all embodiments and constructions of the thermally deformable memory-shaped cuff. These include the following:

(a) It is only required that the alloy material constituting the memory-shaped cuff be thermally deformable on-demand. For convenience and greater facility in achieving such temperature initiated deformity in the degree and at the time required, it is most desirable that the alloy composition forming the cuff be an open weave or meshwork rather than a solid alloy mass, which is considered to be more difficult to deform in a thermally-controlled manner. There is, however, no substantive restriction or limitation at any time or under any intended use circumstances which necessitates an avoidance of a solid mass of material, either as a single alloy sheet or as a laminated plank of alloy material. Accordingly, the choice of whether to use an open meshwork or a solid mass of thermoelastic alloy material is left solely to the discretion of the manufacturer and the surgeon.

(b) The thermoelastic cuff need only be comprised of resilient, flexible, but deformable metallic alloy matter. A number of different alloys of various formulations may be usefully employed when making a deformable memory-shaped cuff suitable for use with the present invention. Among the desirable alloy formulations are those characterized by Table 2 above.

(c) After the deformable cuff has been manufactured using resilient shape-memory alloy materials, the first configured cuff structure (prior to thermal deformation) may be covered to advantage with one or more biocompatible coatings. These biocompatible coatings are intended to water-tighten the article and to facilitate the sewing of the bypass conduit to the cuff as well as to reduce the interactions of the immune system and tissue reaction with the bypass graft after it has been secured to the blood vessels in their appropriate locations in-vivo. Such biocompatible coatings are conventionally known; will reduce the severity and duration of immune or tissue reactions which frequently disrupt or interfere with bypass grafts; and are considered desirable in a majority of use instances in order to minimize the body reaction to vascular bypass surgery. A representative listing of biocompatible coatings deemed suitable for use with the deformable thermoelastic cuff is provided by Table 3 below.

TABLE 3

| Biocompatible Coatings |
| --- |
| High temperature pyrongen-free carbon; |
| Polytetrafluoroethylene (PTFE) and other polyhalogenated carbons; |
| Fibronection; |
| Collagen; |
| Hydroxyethyl methacrylates (HEMA); |
| Serum albumins; and |
| Suprafilm (Genzyme Corp.) |

(d) Although the embodiment of the memory-shaped cuff or collar prior to thermal deformation (exemplified by FIG. 23A) may appear as a geometrically regular and coherent structure, there is no requirement or demand that either the general structure or overall appearance of any configured cuff conform to these parameters. Accordingly, it will be recognized and understood that the deformable, shape-memory alloy cuff structure need not take form as a completely encircling band or collar of thermoelastic material. To the contrary, a U-shaped band or flange of alloy material where the sidewall does not overlap or join and where a gapped distance separates the arms of the band or flange is both permitted and envisioned. Moreover, although the cylindrical-shaped format of the cuff illustrated by FIG. 23 is highly desirable, there is no requirement that the diameter of the cuff prior to or after thermal deformation be constant or consistent over the entire axial length of the cuff. Thus, anisotropic cuff structures as well as isotropic constructions are intended and desirable. In this manner, the cuff in its initial state prior to thermal deformation may have a variable internal diameter over the axial length of the article in which one open end may be either greater or lesser in size than the other open end; and there may be multiple increases and decreases in diameter size successively over the entire axial length of the cuff itself. All of these variations in construction and structure are within the scope of the present invention.

Figure 24B:
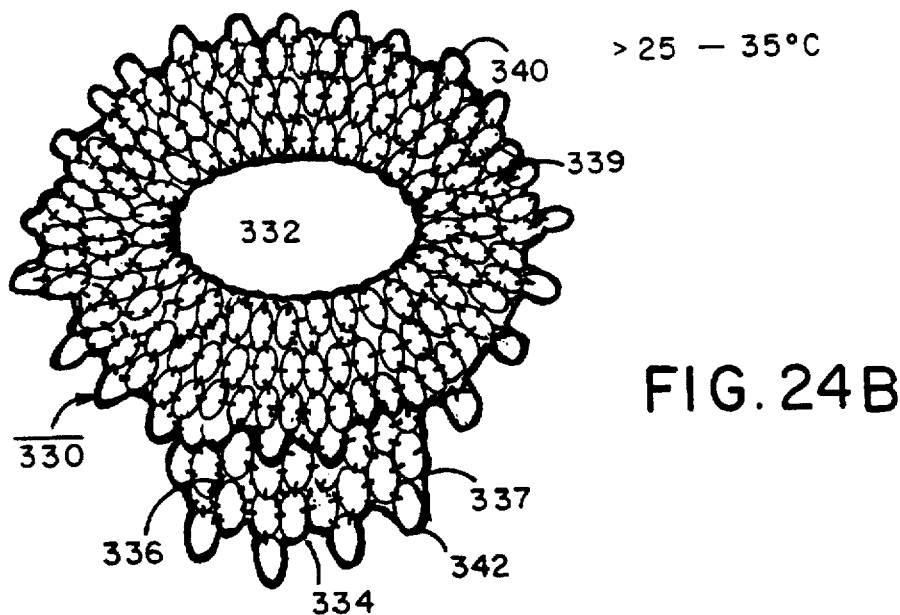
FIGS. 24A and 24B are overhead views of a preferred second deformable cuff in the original undeformed state and the thermally deformed state.
Figure 24A:
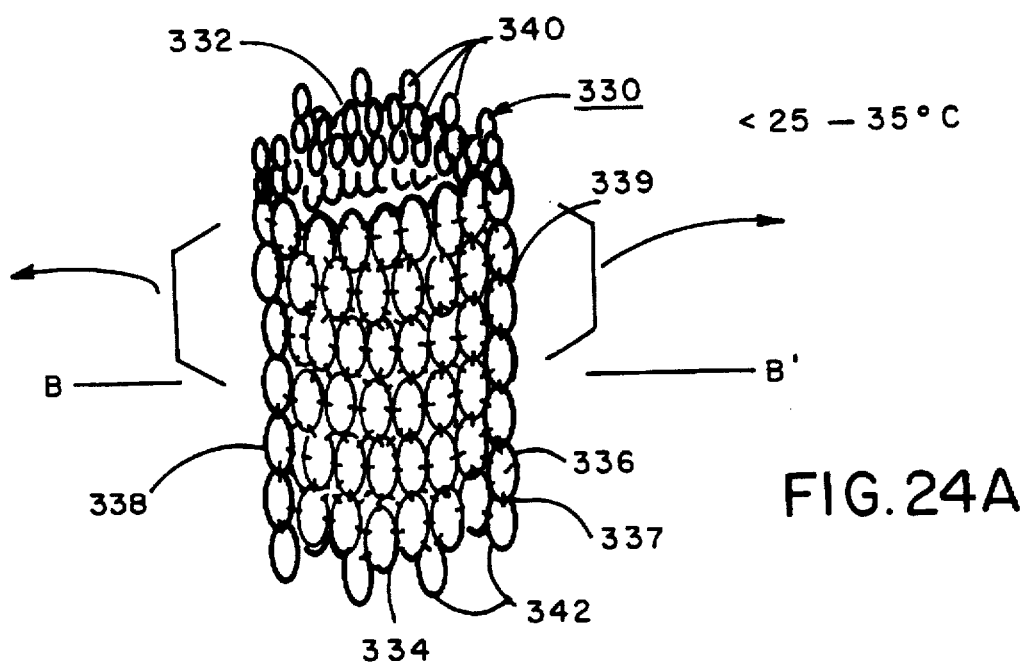

To illustrate some of the modest variations and differences available and envisioned for a deformable thermoelastic cuff intended for use with the present invention, the alternative cuff embodiments illustrated by FIGS. 24, 25 and 26 are provided. As shown within FIGS. 24A and 24B, the first shaped configuration for the deformable cuff or collar 330 appears as a cylindrical-shaped article having two open ends 332, 334 and a rounded sidewall 336. The body of the sidewall 336 is an open meshwork of closed loops 338, each closed loop being joined at multiple points along its perimeter to at least one other closed loop—thereby forming an open grid meshwork. A notable feature of the cuff construction within FIG. 24A is the outer edges of the open ends 332, 334, each of which is formed by a closed loop which is more easily bent and thermally deformed than the closed-loop meshwork in the middle of the sidewall 336. In many instances, the availability of closed-loop edges 340, 342 provide an enormous benefit and advantage when thermal deformation of the cuff occurs in-situ within the internal lumen of an unobstructed artery or vein. In addition, the cuff 330 of FIG. 24A has been memory-shaped to deform substantially at the midline along the axis BB' such that the upper most portion 339 of the cuff near the open end 332 and the edge 340 will deform and flair outwardly as a consequence of placing the cuff in a temperature environment greater than about 25°–35° C.

The result of thermal deformation in-situ at a temperature greater than about 25°–35° C. is shown by FIG. 24B. The sidewall upper portion 339 has become deformed and bent from the open end 332 to about the midline axis BB'. However, the lower sidewall portion 337 has remained substantially unaltered overall its surface area from the midline axis BB' to the other open end 334. This memory-shaped second configuration illustrated by FIG. 24B is the thermally deformed structure suitable for attaching a bypass graft segment to the internal lumen of an artery or vein in-vivo.

Figure 25A:
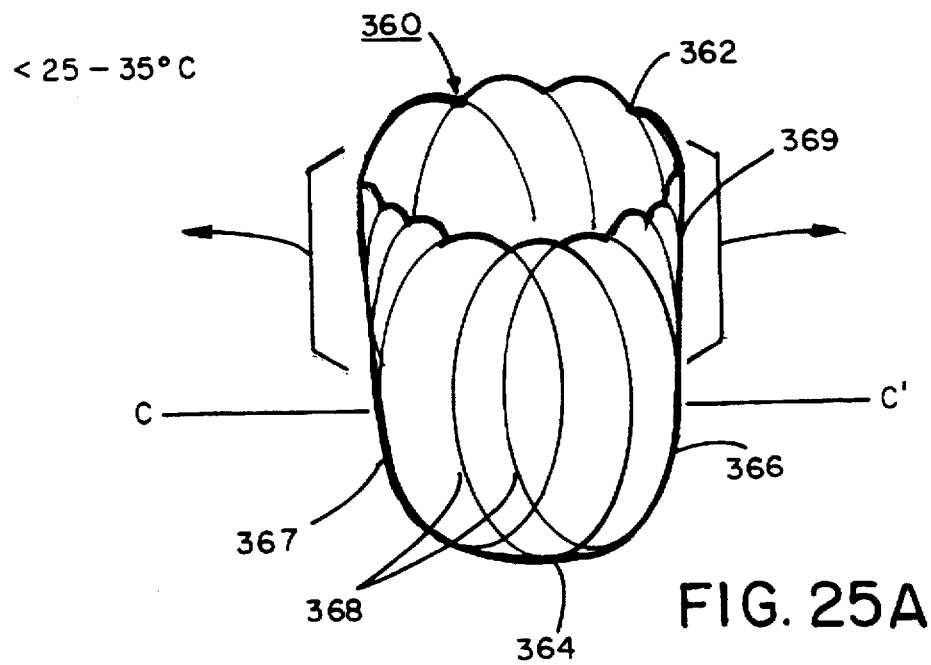
FIGS. 25A and 25B are overhead views of an alternative third deformable cuff in the original undeformed state and the thermally deformed state.

A third embodiment of a thermally deformable cuff or flange is illustrated by FIGS. 25A and B. As shown therein, the first configuration for the deformable cuff 360 illustrated by FIG. 25A and is formed primarily as a series of coiled wires 368 whose overlapping and intersecting junctures have been fused together to make a coiled unitary article. The deformable cuff 360 at temperatures less than about 25° C. thus has two open ends 362, 364 and an open coiled sidewall 336 formed from the commonly fused coils of wire. The open lattice work of coiled wires 368 provides the flexible and resilient meshwork suitable for achieving the primary functions of the memory-shaped deformable cuff. The sidewall 366 also has been pre-stressed along the middle axis CC' such that the uppermost sidewall portion 369 will become bent and deformed outwardly when exposed to an environmental temperature greater than about 25°–35° C.

Figure 25B:
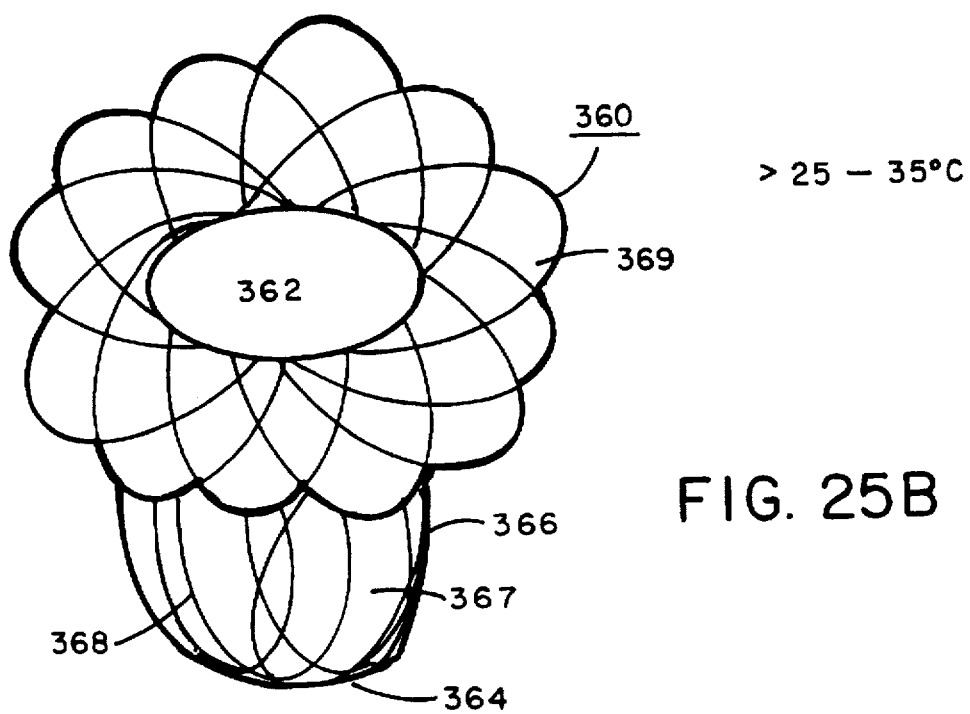

The consequence of placing the coiled cuff 360 in an ambient temperature greater than about 25°–35° C. is shown by FIG. 25B. It will be appreciated that the second, memory-shaped configuration of FIG. 25B is intended to be an in-situ generated result, occurring typically within the internal lumen of an artery or vein in-vivo. Thus the flaired out uppersidewall portion 369 has become bent at nearly a 90 degree angle with respect to the lower sidewall portion 367; and the midline CC' will generally serve as the axis of thermal deformation and curvature for the coiled cuff 360.

Figure 26A:
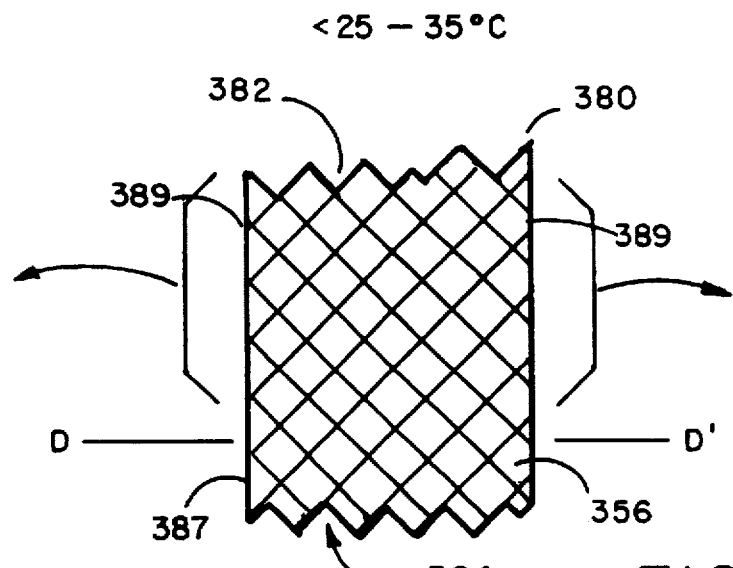
FIGS. 26A and 26B are overhead views of an alternative fourth deformable cuff in the original undeformed state; and the thermally deformed state.
Figure 26B:
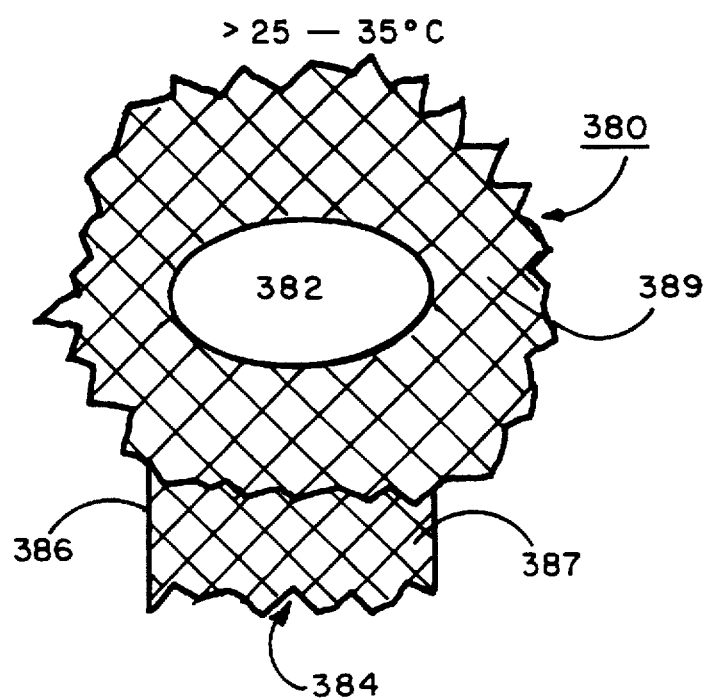

Finally, a fourth alternative embodiment is provided by FIGS. 26A and 26B in which a thermally deformable cuff or band 380 in the first configuration is shown having two open ends 382 and 384. In this instance, however, the sidewall 386 of the cuff 380 is comprised of a solid sheet of material. Two other features are also included in this embodiment of the thermally deformable cuff due to its construction using a solid sheet of resilient material as the sidewall 386 for the cuff. The sidewall 386 has been preferably pre-scored to form cross-hatched squares over the axial length of the sidewall; and the pre-scored sidewall thus will deform far more easily and bend outwardly along the scored lines of demarcation as shown when the cuff is placed in an ambient temperature greater than 25°–35° C. Similarly, the sidewall material has been pre-stressed along the midline axis DD' such that the upper most region 389 nearest the opening 382 will become bent far more easily and deform in a controlled fashion when and as required by the user.

The effect and consequences of disposing the cuff 380 in an ambient environment whose temperature is greater than about 25°–35° C. is shown by FIG. 26B. The uppermost sidewall portion 389 has thermally deformed into the memory-shaped second configuration; and become bent into a curved lip extending outwardly from the midline axis DD'. However, the lower sidewall portion 387 of the cuff 380 has remained substantially unchanged from its initial shape and size. The memory-shaped characteristics have thus generated an in-situ thermal deformation most suitable for the attachment of a bypass graft in-vivo.

II. The Bypass Graft Material

Two major sources of conduits suitable for use as a bypass graft are presently known and available. These are: synthetic prosthetic channel sections and previously excised blood vessel segments.

The choice of graft conduit it crucial to the success of coronary artery bypass grafting surgery (CABG) because the patency of a coronary conduit is closely associated with an uneventful postoperative course and a better long-term patient survival. The standard vascular conduits used for CABG are excised blood vessel segments taken from the greater saphenous vein (GSA) or another leg or arm vein. An excellent substitute conduit for coronary bypass operations that can be available on demand is certainly the desire of every practicing cardiac surgeon. However, virtually every synthetic alternative to arterial conduits or autologous fresh saphenous vein conduits has proved disappointing. Fortunately, patients with absolutely no autologous conduit are uncommon. Circumstances exist, however, that often necessitate the use of alternative synthetic conduits such as young hyperlipemic patients; as absent or unsuitable autologous internal mammary artery and greater saphenous vein as a result of previous myocardial revascularization, peripheral arterial reconstruction; and varicose vein ligation procedures. In the present era of increasing numbers of repeat coronary revascularizations, approximately 15% of patients requiring CABG are now in need of alternative synthetic conduits.

A. Synthetic Conduits

The desired characteristics of synthetic conduits used as bypass grafts are nonimmunogenicity, easy availability and storage, less risk of kinking (due to its stiffness), a less turbulent flow (due to uniform diameter), and an absence of branches.

The medical value of synthetic conduits as bypass grafts in-vivo has been substantially investigated. See for example: Foster et. al., *Circulation* 79 *(Sup* 1): 134–139 (1989); and Canver, C. C., *Chest* 108: 1150–1155 (1995); and the other references cited below. A summary review of the recent reports evaluating these conduits thus is in order.

Historically, Sauvage and associates in 1976 [*J. Thorac. Cardiovasc. Surg.* 72: 418–421 (1976)] described the placement of a 4.0-cm long, 3.5-mm diameter knitted Dacron flamentous vascular prosthesis as an interposition graft between the aorta and right coronary artery during repair of a vascular aneurysm of the ascending aorta in an adult. The graft was demonstrated to be patent by angiography 16 months after operation. A literature search at the time found only two other prior reports of successful aortocoronary grafting with synthetic conduits, both involving children with congenital coronary defects. Two factors present in all three cases that were suggested as promoting long-term patency were that only short segments of prosthetic graft were placed, and that they were implanted as interposition grafts from the end of the coronary artery to the aorta.

The initial results of CABG with expanded polytetrafluoroethylene (PTFE) (Gore-Tex. W. L. Gore and Associates, Elkton, Md.) grafts were encouraging; however, this impression was based on single-case reports or series with small numbers of patients. Molins and co-authors in 1978 [*J. Thorac. Cardiovasc. Surge.* 75: 769–771 (1978)] presented a patient in whom they had constructed a bypass to the distal right coronary artery with a 4.0 mm diameter PTFE graft, found patent on catheterization 3 months after surgery. Also, Yokoyama and associates in 1978 [*J. Thorac. Cardiovasc. Surg.* 76: 552–555 (1978)] described five aortocoronary bypass patients in whom 3.0–5.0-mm PTFE grafts had been used. Four of five of these grafts were open on restudy 3–6 months postoperatively. Subsequently, Islam and colleagues in 1981 [*Ann. Thorac. Surg.* 31: 569–573 (1981)] reported that a 6-mm diameter PTFE graft used for aorta-to-right coronary artery bypass remained widely patent on repeat angiography 18 months after surgery.

An indication of the early and midterm results of CABG with PTFE grafts was provided in the 1981 report of Sapsford and associates [*J. Thorac. Cardiovasc. Surg.* 81: 860–864 (1981)]. Twenty-seven coronary bypasses were constructed in 16 patients with 4.0-mm PTFE grafts. Eleven patients were restudied at 3 months after surgery, and a 61% (11 of 18) graft patency rate was found, in six patients who had repeat angiography 12–29 months after CABG, six of nine PTFE grafts were open. Then, Murta and co-authors in 1985 [*Ann. Thorac. Surg.* 39: 86–87 (1985)] detailed a single case experience where two 4.0-mm diameter PTFE aortocoronary grafts remained present 53 months postoperatively. More recently, Chard and associates reported in 1987 [*J. Thorac. Cardiovasc. Surg.* 94: 132–134 (1987)] long-term patency results with PTFE aortocoronary grafts. Using both one-to-side and multiple, sequential, side-to-side anastomoses, they constructed a total of 28 distal coronary grafts in eight patients. Patency rates on repeat angiography were 64% (18 of 28) at 1 year, 32% (9 of 28) at 2 years, 21% (6 of 28) at 3 years, and 14% (4 of 28) at 45 months.

The choices of materials recognized as being suitable for the making of a biocompatible synthetic conduit are quite limited. These are provided by Table 4 below.

B. The Excised Blood Vessel Segment

A variety of blood vessel segments excised from the vascular system in-vivo are suitable for use as bypass graft conduits. A representative, but incomplete, listing is provided by Table 5 below.

TABLE 4

Synthetic Conduit Materials

Synthetic Substances

Dacron (knitted or woven) polymer;
Polytetrafluoroethylene or "PTFE" (knitted or woven);
Impra;
Teflon polymer; and
Kevlar polymer.

TABLE 5

Vascular Conduits For Bypass Grafting

Venous Conduits (a). Autologous vein conduits.
  Greater saphenous vein segments;
  Lesser saphenous vein segments;
  Upper extremity (cephalic and basilic) vein segments.
(b). Nonautologous vein conducts.
  Umbitical vein segments;
  Greater saphenous vein homografts.

Arterial Conduits (a). Autologous arterial conduits.
  Internal mammary artery segments;
  Right gastroepiptoic artery segments;
  Inferior epigastric artery segments;
  Radial artery segments;
  Splenic artery segments;
  Gastroduodenal artery segments;
  Left gastric artery segments;
  Intercostal artery segments.
(b). Nonautologous arterial conduits.
  Bovine internal thoracic artery segments.

The preferred sources of blood vessels suitable for use as a vascular bypass graft are the saphenous veins. These veins constitute the superficial veins of the lower extremities and comprise both the greater (or long) saphenous and the lesser (or short) saphenous veins. Anatomically, the long saphenous vein begins on the medial side of the foot and ends in the fermoral vein below the inguinal ligaments; and the short saphenous vein begins behind the lateral malleous and runs up the back of the leg to end in the popliteal vein. However, if the saphenous veins of the particular patient are unsuitable or unavailable for any reason, either the cephalic or the basilic veins are very acceptable substitutes for use as a vascular bypass conduit. However, if these leg or arm veins are not available, synthetic or other biologic materials may also be used as substitutes.

The medical procedure to isolate and excise the saphenous vein of choice is conventionally known and considered a routine surgical technique. The saphenous vein is harvested under general anesthesia. An incision is first made in the medial malleolus, where the saphenous vein is often dilated. The saphenous vein is identified and then dissected with a single incision made along its course with scissors. Branches are doubly clamped with hemostatic clips and divided. The saphenous vein is then freed up and removed from the leg. The leg wound is closed with subcutaneous sutures and Steristrip adhesive over the incision. The vascular segment is prepared on a separate sterile table with adequate light and loupes, and branches are selectively ligated with 4–0 silk. An oval-tip needle on a syringe is inserted into the graft to gently dilate it by administering a balanced electrolyte solution (pH 7.4, chilled to 7° to 10° C.) and 10,000 units/liter of heparin. A valvulotome is inserted into the vein graft segment and the valves clipped with a 3-mm right-angle stainless steel instrument with a highly polished ball tip on the right angle. The knife edge is protected and sharply splits the cusp, causing valvular incompetence. Measurements for the approximate lengths of the grafts may be made with umbilical tapes, and the appropriate lengths may be chosen before it is sewn to the cuff and coronary arteries.

III. The Introducer System

The introducer system comprises the catheter apparatus including the thermoelastic deformable cuff and a bypass conduit in combination; and it is this introducer system which is utilized by the surgeon to perform the requisite acts and manipulations by which the bypass conduit is delivered to and becomes secured within the lumen of the unobstructed major blood vessel (and subsequently anastomosed to the obstructed blood vessel at a site distal to the obstruction). For descriptive purposes and for increased clarity of comprehension, this description will intentionally limit itself to the use of the variable-sized obturator illustrated by FIGS. 9 and 10 respectively; to the thermally deformable cuff structure illustrated previously by FIGS. 23A and 23B respectively; and to the use of a previously excised vascular segment taken from the long or short saphenous vein in the same patient. The introducer system represents and provides for the intentional placement and carriage of the bypass conduit on the obturator, the engagement and juncture of the deformable cuff to one end of the bypass conduit prior to grafting in-vivo; and the proper orientation of the then engaged cuff/bypass conduit together on the obturator with respect to its relationship to the puncturing headpiece.

The preferred introducer system begins with the proper placement of a previously excised vascular segment (desirably taken from the saphenous vein) upon the obturator. This initial manipulation is illustrated by FIG. 27 in which a previously excised vascular segment 400 having two open ends 404 and 406 is placed upon the elongated shaft 134 adjacent to but preferably not in direct contact with the base plate 126 of the puncturing headpiece 122 of the obturator (previously shown by FIGS. 9 and 10 respectively). As shown by FIG. 27, it is intended and preferred that the elongated shaft 134 be inserted at the proximal end 138 into the internal lumen 402 of the excised vascular segment 400 by the surgeon; and that the body of the vascular segment 400 (comprising the portions 410 and 412) then be conveyed over the axial length of the elongated shaft 134 until the open end 404 and vascular portion 410 are at a chosen position, typically 1-2 centimeters from the distal end adjacent to the puncturing headpiece 122. In this manner, the weight and body of the excised vascular segment 400 is carried on the elongated shaft 134; and it is desirable that the diameter of the elongated shaft 134 be smaller than the overall diameter of the internal lumen 402 for the vascular segment 400. As a consequence of this placement, the excised vascular segment is adequately supported, carried, and transported by the elongated shaft during the entirety of the manipulations prior to entry into the body of the living patient as well as subsequent to the in-vivo perforation of the unobstructed major artery or vein. The manipulation illustrated by FIG. 27 is expected to be performed by the surgeon immediately after excising the vascular segment from the patient but prior to beginning the bypass graft surgery itself.

After the excised vascular segment 400 has been properly positioned on the elongated shaft 134 of the obturator 120, the deformable cuff 300 (illustrated by FIG. 23 and described in detail previously herein) is desirably passed over the puncturing headpiece 122 and over the open end 404 to cover the small portion 410 of the exterior surface over of the excised vascular segment 400. This is illustrated by FIG. 28. It is desirable (but not absolutely necessary) that a gap distance "g" (about 1-2 centimeters) separating the open end 404 from the puncturing headpiece 122 be maintained during the placement of the deformable cuff—as this will allow for easier positioning of the thermally deformable cuff in a pre-chosen alignment and posture and in a more controlled manner of deformation on-demand.

When the deformable cuff has been positioned over the vascular segment to the satisfaction of the surgeon, the lower sidewall portion 307 of the cuff covering the exterior surface 410 nearest the open end 404 of the excised vascular segment 400 must be physically engaged and become joined to the vascular segment in a reliable and safe manner. This is also illustrated by FIG. 28. One preferred manner of engagement and juncture is for the surgeon to suture the open meshwork sidewall 306 of the cuff 300 directly to the portion 410 of the excised segment 400. This suturing is easily performed by the surgeon prior to beginning the grafting surgery and each of the sutures 420 will serve as the physical means for engaging and permanently joining a portion of the open meshwork of wires in the sidewall of the cuff to the excised vascular segment itself. The type of sutures 420, their placement, their number, and the linkage to the vascular wall of the excised segment are left to the personal discretion and choice of the surgeon.

Other means for permanent engagement and juncture of the thermally deformable cuff to the vascular wall of the excised segment also are commonly available. These include surgical staples; biocompatible adhesives; encircling ligatures; and a wide range of surgical fasteners and closures. Any and all of these alternatives may be employed alone or in combination to achieve a reliable engagement and juncture.

One optional variation of the introducer system provides that the open meshwork sidewall 306 of the cuff 300 can be covered with synthetic materials to facilitate the suturing, stapling or other means for attaching the prosthetic channel section or vascular segment to the cuff. These biocompatible synthetic materials can be applied in one or more layers or coatings to the cuff; and serve as an overlay for a portion or the entirety of the cuff sidewall.

In addition, another optional variation of the introducer system allows the sidewall of the cuff to be positioned within the lumen of the prosthetic channel section or excised vascular segment. In these instances, the meshwork sidewall of the cuff is incorporated within the interior of the prosthetic conduit or vascular bypass segment in order to eliminate the need for direct sewing of the bypass conduit to the cuff. This variant thus offers a simplified procedure for locking the cuff to the bypass conduit in a permanent fashion.

After the deformable cuff 300 has been engaged and joined to one end of the excised vascular segment 400 then carried upon the elongated shaft 134 of the obturator, the size of the puncturing headpiece 122 should be adjusted in shape and girth such that the diameter of the base plate 126 of the puncturing headpiece 122 preferably is equal to or slightly greater than the diameter of the open cuff end 302. This manipulation is also illustrated by FIG. 28 where the size of the base plate 126 is coextensive in diameter with the diameter of the open end 302 of the deformable cuff. In this preferred manner, the entirety of the puncturing headpiece 122 serves as a front section or first stage for the introducer system as a whole.

Figure 29:
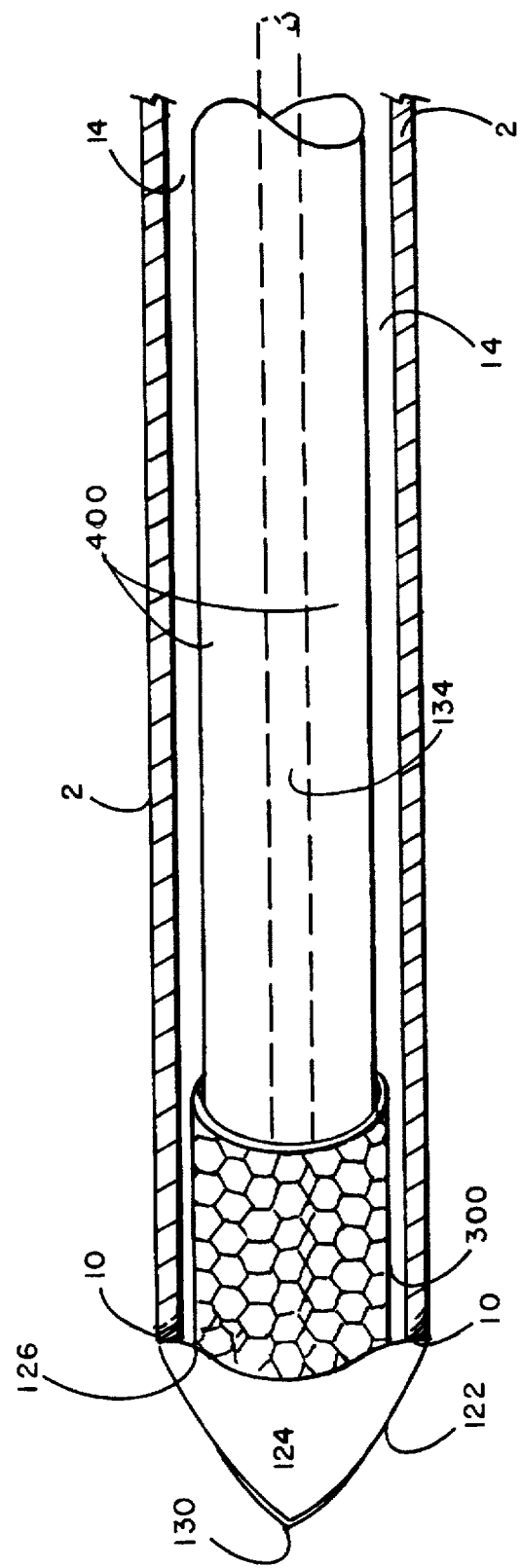
FIG. 29 is a partially exposed view of the introducer system as a whole.

The complete introducer system is illustrated by FIG. 29 in which the fully prepared obturator carrying the previously excised vascular segment to be used as a bypass conduit and the thermally deformable cuff have been positioned in advance; and the prepared obturator has been placed within the internal lumen of a catheter. As seen therein, the catheter appears in an exposed, cross-sectional view and shows the hollow tube 2 of fixed axial length having a discrete proximal end (not shown), a discrete distal end 10 and an internal lumen 14 of pre-determined diameter sufficient to house the entirety of the prepared obturator (illustrated by FIG. 28). The distal end tip 10 of the catheter is adapted for direct delivery of the catheter in-vivo to a chosen site where an unobstructed artery or vein is in anatomic proximity to an obstruction lying within another blood vessel; and the prepared obturator of FIG. 28 (comprising the previously excised blood vessel segment and the deformable cuff) lies within the internal lumen 14 of the catheter. The introducer system shown by FIG. 29 is complete; and the surgeon may now begin the first steps for surgically delivering the introducer system into the thoracic cavity or other appropriate body region in order to create the bypass graft.

Maintaining the ambient temperature of the internal lumen of the catheter at less than about 25°–35° C.

The preferred means for cooling and maintaining the temperature of the internal lumen in a guiding catheter comprising the introducer system at less than about 25°–35° C. during the creation of a bypass graft in-vivo is via the use of cold physiological-strength (0.85–0.9%) saline. Typically, a sterile saline pack is refrigerated in advance of the repair surgery and cooled to a temperature between 40°–50° F. (5°–10° C.). The cooled saline is then infused by the surgeon into the internal lumen of the catheter in order to cool the thermally deformable cuff both initially and periodically during the surgery. The sterile saline is compatible with the living tissue of the patient; and multiple applications of saline can be introduced into the internal lumen volume of the catheter as often as deemed necessary without meaningful risk to either the introducer system or the patient.

As an alternative to the use of saline infusion, any other suitable means for cooling (such as gaseous carbon dioxide) may also be employed as a less preferred practice for maintaining the environmental temperature of the internal lumen volume of a catheter at less than about 25°–35° C. Such alternative procedures, however, are often less desirable due to the effects of potential direct contact and possible biological reaction when intentionally or inadvertently released into the bloodstream or other highly vulnerable organs and tissues of the body. Nevertheless, the use of alternative means to reduce the environmental temperature of the internal lumen volume of a catheter to less than about 25°–35° C. can be safely and properly performed in many different medical circumstances using the present invention.

IV. The Routing And Surgical Introduction Of The Controlling Catheter Into The Body Of The Living Human Catheterization involves a great deal of technical skill, some instrumentation and mature judgment in order to choose among the appropriate procedures and the various techniques which are now conventionally known and available for use. Clearly, because the present technique constitutes catheter intervention in critically ill patients, the physician or surgeon must be very familiar with the available anatomical alternatives in order to select the best routing for introducing the catheter, the best technique in order to access the thoracic cavity of the body where the obstructed artery and aorta exist, and to carefully select the timing and other operative conditions in order to achieve best results.

In general, catheterization can be performed using any duct, tube, channel, or passageway occurring naturally or surgically created for the specific purpose. Thus, among the naturally occurring passageways in the body are the anus; the alimentary canal; the mouth, ear, nose, or throat; a bronchus of the lung; the urethra; the vaginal canal and/or cervix; and any blood vessel of sufficient size of the central circulation in the body. Any of these routings are envisioned and expected to be used when and if appropriate. However, clearly a commonly used and the critical route of access is the introduction of catheters into the thoracic cavity and the arterial blood circulation adjacent to the heart.

For this reason, it is useful to briefly summarize the technique currently in use for introduction of catheters into the central blood circulation as an illustrative example of preferred catheterization techniques. There are two general methods currently in use. These are: (a) percutaneous introduction using needles and guidewires; and (b) direct introduction after surgical isolation of the blood vessel of choice. While either general method may be utilized at any site of the general circulation, practical and anatomical considerations will generally dictate which approach is most appropriate under the individual circumstances.

The modified Seldinger Technique

Figure 30A:
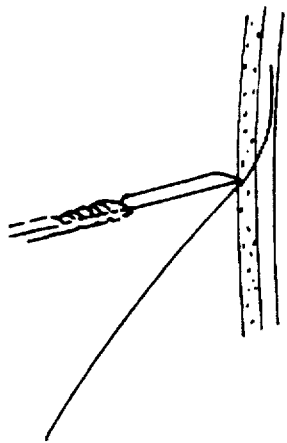
FIGS. 30A–30F are illustrations of the modified Seldinger technique conventionally used for percutaneous catheterization.
Figure 30B:
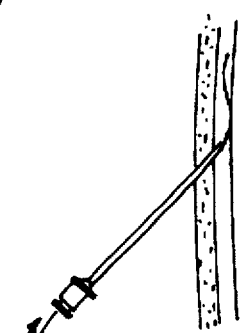
Figure 30C:
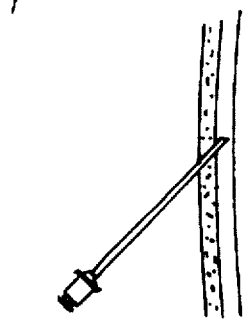
Figure 30D:
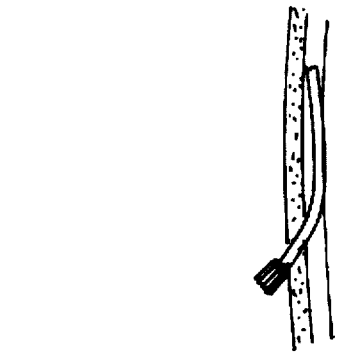
Figure 30E:
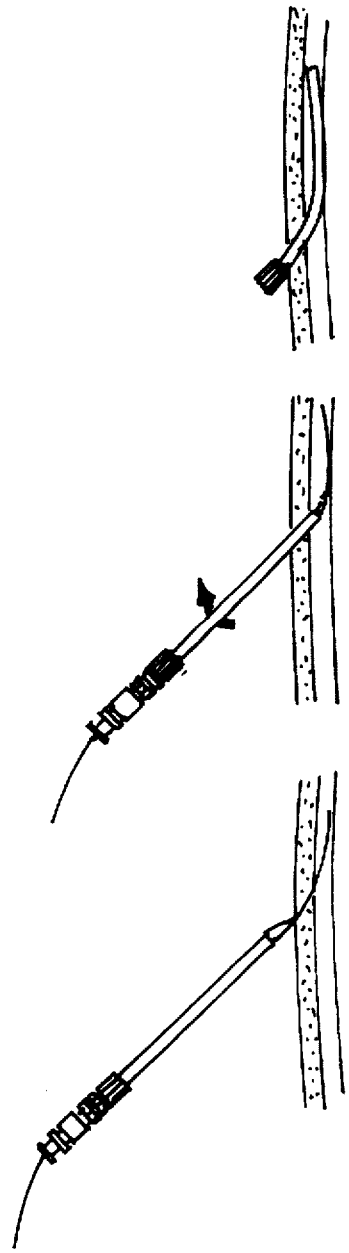
Figure 30F:
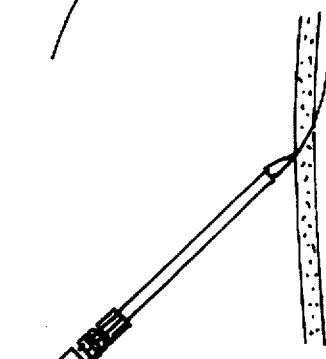

The percutaneous introduction of a catheter is illustrated by the modified Seldinger technique which is shown by FIGS. 30A–30F respectively. FIG. 30A shows a blood vessel being punctured with a small gauge needle. Once vigorous blood return occurs, a flexible guidewire is placed into the blood vessel via the needle as shown by FIG. 30B. The needle is then removed from the blood vessel, the guidewire is left in place, and the hole in the skin around the guidewire is enlarged with a scalpel as shown by FIG. 30C. Subsequently, a sheath and a dilator is placed over the guidewire as shown by FIG. 30D. Thereafter, the sheath and dilator is advanced over the guidewire and directly into the blood vessel as shown by FIG. 30E. Finally, the dilator and guidewire is removed while the sheath remains in the blood vessel as illustrated by FIG. 30F. The catheter is then inserted through the sheath and fed through to reach the desired location.

The other general method for the introduction of catheters into the blood circulation is a direct surgical cutdown. Cutdown procedure is often a complex invasive surgery and is used only no direct access is generally available. A far more complete and fully descriptive review of both these general catheterization techniques is provided by the texts of: *Diagnostic And Therapeutic Cardiac Catheterization*, second edition, 1994, Chapter 8, pages 90–110 and the references cited therein.

Accordingly, for purposes of practicing the present methodology, any and all conventionally known general catheterization procedures and techniques which are conventionally known and in accordance with good medical practice are explicitly intended to be utilized as necessary in their original format or in a modified form. All of these general catheterization routing and use techniques are thus envisioned and are deemed to be within the scope of the present invention.

31

General rules for choosing an appropriate site of body entry

An axiomatic or general set of rules by which a surgeon or radiologist can chose a proper or appropriate site of entry for introducing the guiding catheter into the body of a patient for purposes of creating a vascular bypass in-vivo is as follows: (a) always pick the shortest and straightest pathway possible or available; (b) identify the chosen entry site on an existing and accessible unobstructed artery or vein, the larger the diameter of the unobstructed artery or vein the better; and (c) identify the location and orientation of the obstruction in the obstructed artery or vein and chose an entry site distal to the obstruction.

A favored approach to introducing the guiding catheter into the thoracic aorta

Using the ascending aorta approach as a representative illustration and example:

(1) Under general anesthesia, the chest of the patient is prepared and draped in a sterile fashion.

(2) A three-inch incision is made to the left or right of the breast bone through which the surgeon operates.

(3) Three additional one-inch incisions then are made to insert a video camera, knife, surgical stapler, and other instruments.

(4) The ribs are separated, the thoracic cavity is entered, and the ascending thoracic aorta is exposed.

(5) The introducer system is then positioned at the chosen site on the ascending thoracic aorta.

V. The In-Vivo Placement Of The Vascular Bypass Graft Into The Lumen Of The Unobstructed Major Blood Vessel The method of the present invention utilizes the introducer system via the catheterization technique to create a bypass graft conduit between a major unobstructed blood vessel such as the aorta and an obstructed blood vessel in-vivo using a previously excised vascular segment as a conduit. This procedure is illustrated by FIGS. 31–39 collectively. It will be recognized and appreciated, however, that while FIGS. 31–39 exemplify and illustrate the manipulations of the surgeon and the events in sequence leading to the creation of a vascular bypass, this description and the figures themselves present a greatly simplified presentation and explanation of the medical procedure, the technical skills required, and the safety measures taken for the patient's benefit medically. The use of synthetic conduits and fixed-size obturators, although not described, is also within the scope of the present methodology.

Figure 31:
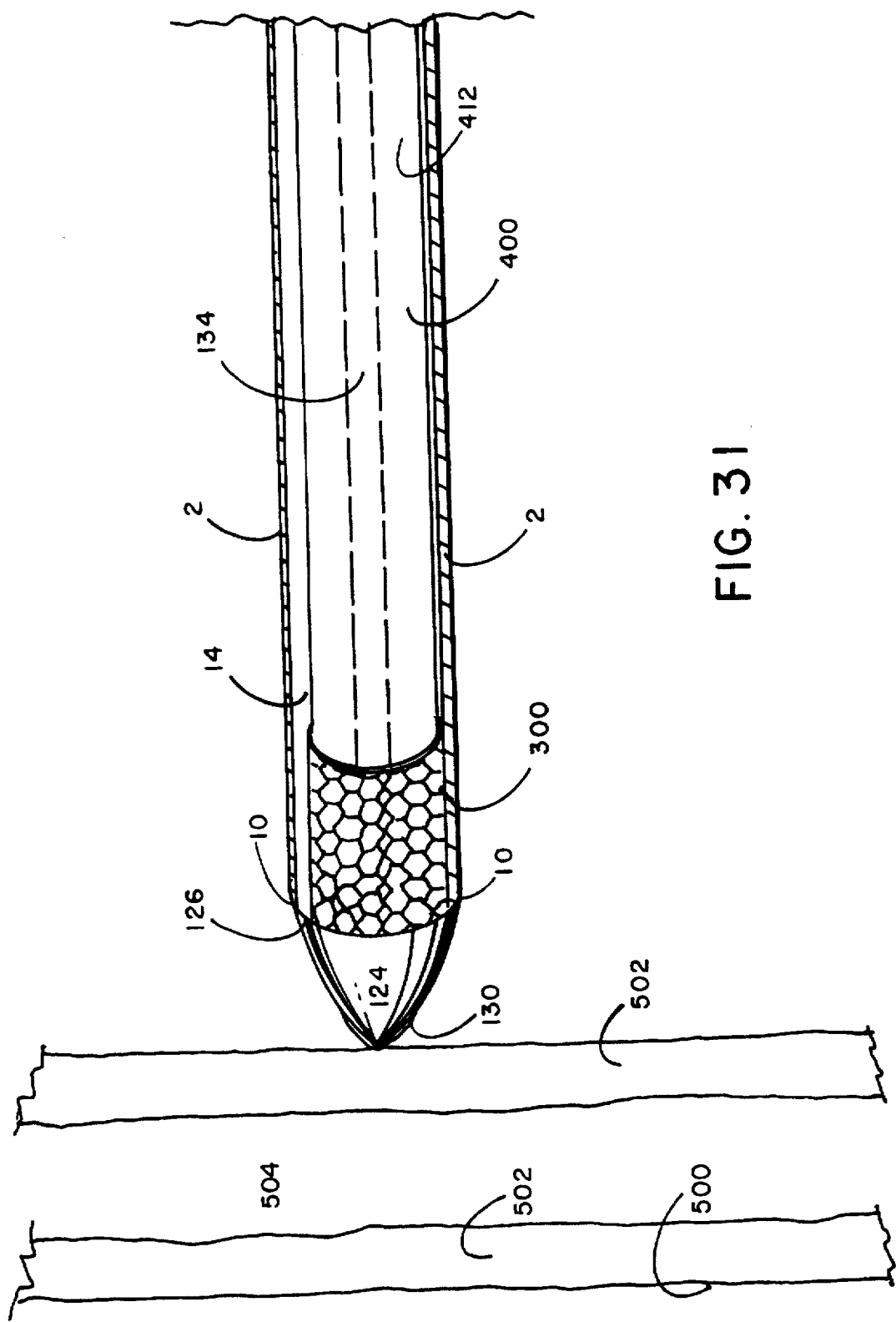
FIG. 31 is a partially exposed view of the introducer system in the correct position at the exterior wall of an unobstructed blood vessel in-vivo.

After the introducer system catheter has been routed and surgically delivered into the body of the living human in the manner described previously herein, the first stage for the process is reached as shown by FIG. 31. The illustration of FIG. 31 (as well as FIGS. 32–40 respectively) are shown as partially exposed views in order to show more easily the detailed placement and orientation of the introducer system comprising the prepared obturator carrying the thermally deformable cuff and previously excised vascular segment in combination.

As seen within FIG. 31, a major artery such as the aorta 500 is shown in partial cross-sectional exposed view to reveal the thickness of the arterial wall 502 and the internal lumen 504. The catheter and the prepared obturator comprising the introducer system are as described in detail previously herein and illustrated by FIG. 29. It will be noted that the puncturing headpiece 122 of the obturator 120 is positioned within the lumen of the catheter such that the perforating end tip 130 is in direct contact with the arterial

32 wall 502 at the chosen anatomic site. The puncturing headpiece 122 is of sufficient size such that the entirety of the thermally deformable cuff 300 and the joined vascular segment 400 lie directly behind and are in axial alignment with the puncturing headpiece 122 and the elongated shaft 134. When positioned as shown by FIG. 31, the prepared obturator has been cooled to a temperature less than about 25° C. (using cold saline or gaseous carbon dioxide), and is properly placed for piercing and penetrating the arterial wall on-demand.

Figure 32:
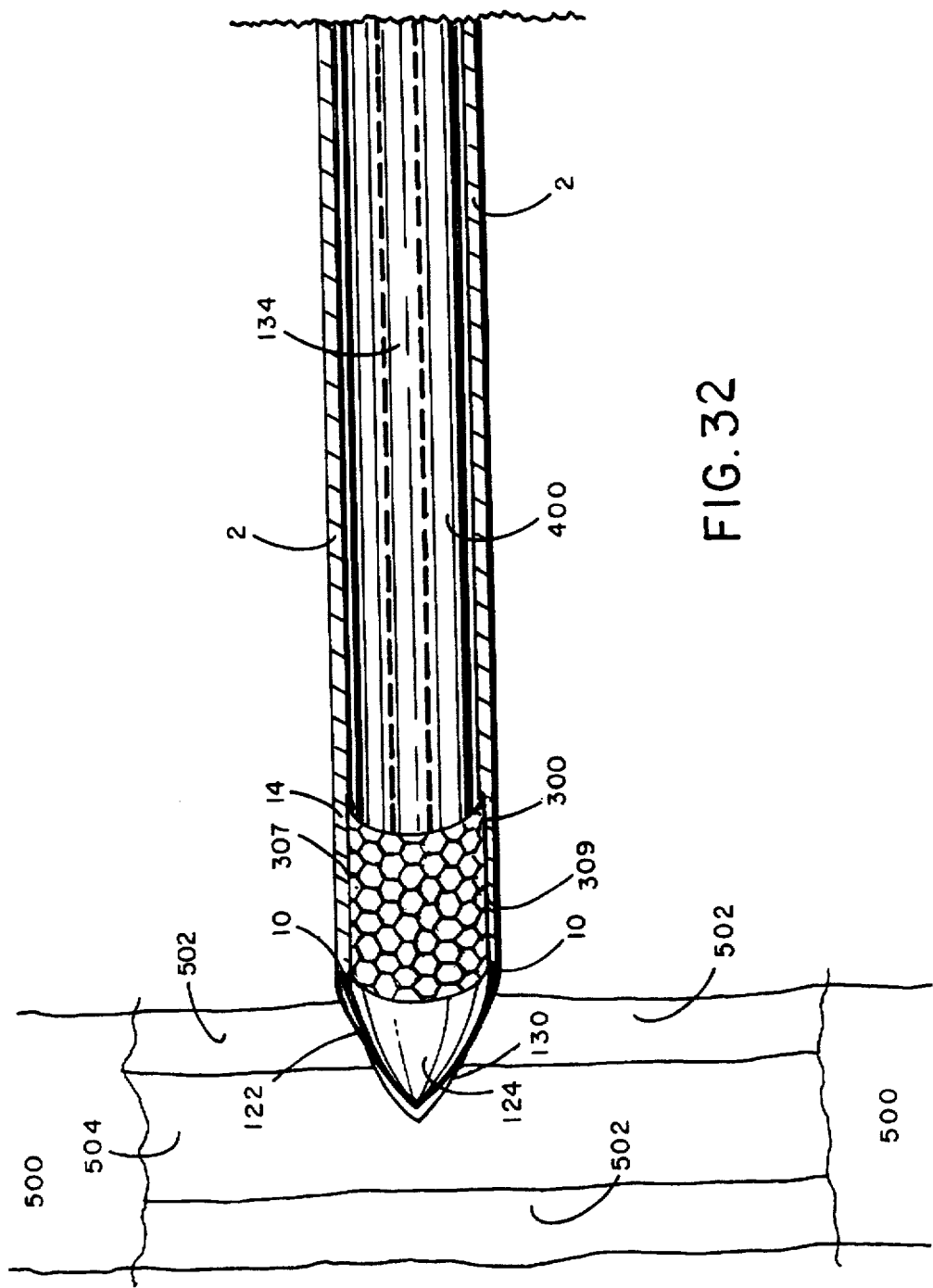
FIG. 32 is a partially exposed view of the introducer system penetrating the vascular wall of the unobstructed blood vessel in-vivo.

When the surgeon extends the prepared obturator within the cooled and temperature controlled internal lumen of the catheter, the result is illustrated by FIG. 32. As seen therein, the perforating end tip 130 has punctured and pierced through the arterial wall 502; and been advanced into the arterial lumen 504. The initial pierced hole in the arterial wall 502 made by the perforating end tip 130 is widened into a passageway as a consequence of the entire puncturing headpiece 122 following the entry path created by the perforating end tip. As the puncturing headpiece 122 penetrates through the arterial wall 502, the size of the puncture in the arterial wall becomes widened and enlarged to conform to and accommodate the configuration and the girth of the puncturing headpiece in its entirety. The configuration and overall size of the puncturing headpiece 122 thus serves as the means for enlarging the initial puncture made by the perforating end tip 130 such that the entire girth and overall diameter of the obturator (complete with thermally deformable cuff and excised blood vessel segment in combination) can subsequently pass through the enlarged hole in the arterial wall.

Figure 33:
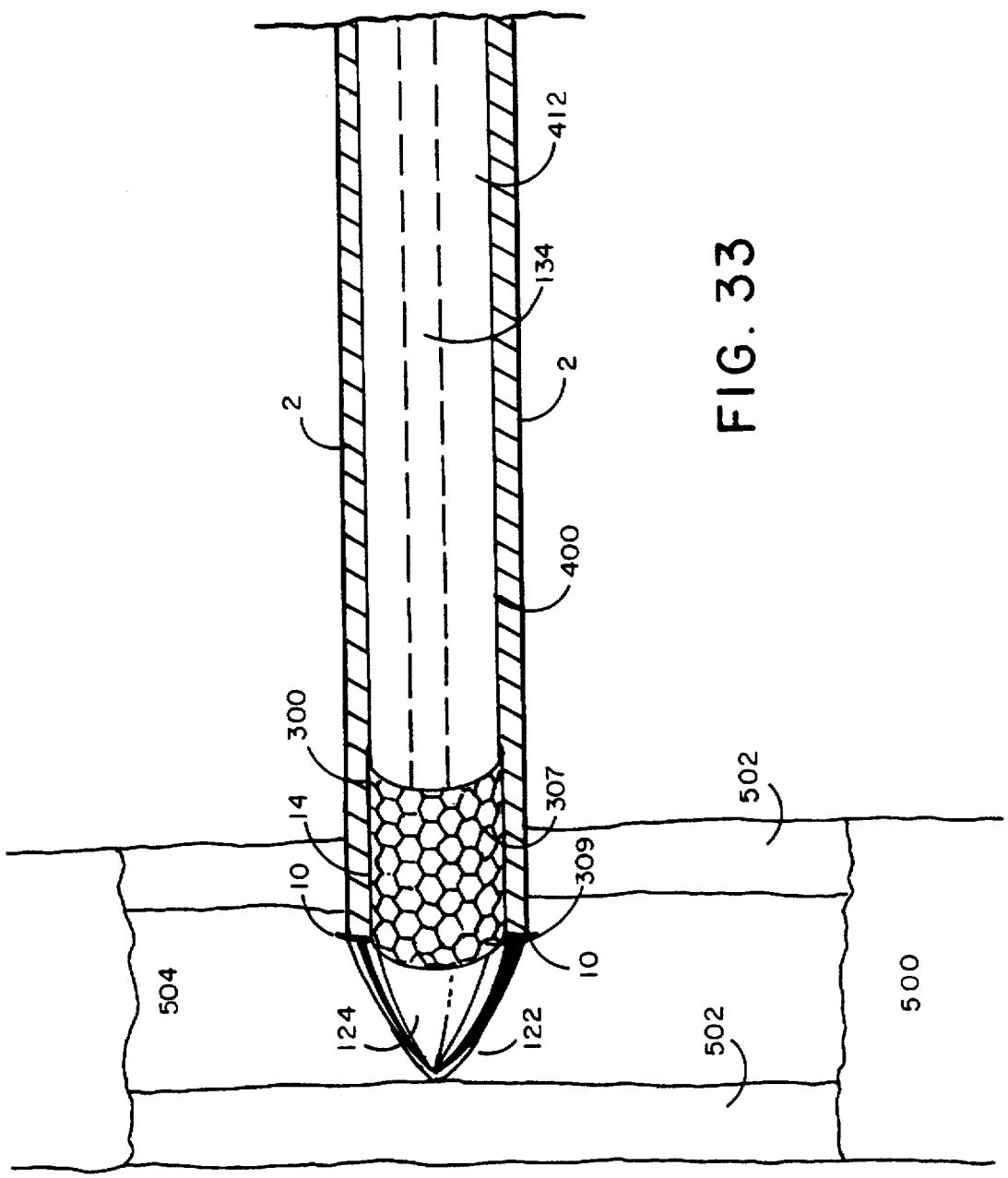
FIG. 33 is a partially exposed view of the introducer system within the internal lumen of the unobstructed blood vessel in-vivo.

As the prepared obturator is extended further across the thickness of the arterial wall 502 through the enlarged passage, the penetrating headpiece 122 is desirably extended farther into the arterial lumen 504 until at least the upper sidewall portion 309 of the thermally deformable cuff 300 also has been advanced far enough to lie within the internal lumen of the blood vessel. This sequence of events and result is illustrated by FIG. 33.

Then the surgeon slowly and carefully withdraws the catheter 2 from the passageway in the arterial wall 502 while maintaining the components of the prepared obturater in a stationary position. Consequently, the upper sidewall portion 309 of the cuff 300 is slowly released into the arterial lumen 504 from the internal lumen 14 of the receding catheter 2 and the thermoelastic alloy comprising the cuff 300 begins to deform in-situ into the second memory-shaped configuration. This manipulation and result is illustrated by FIG. 34.

As seen therein, the surgeon has activated the means for contracting the girth of the puncturing headpiece; and partially withdrawn the catheter such that the uppermost part of the cuff has been released into the warm temperature environment of the arterial lumen in-vivo. Thus FIG. 34 shows the beginning of thermal deformation for the cuff in-situ within the arterial lumen.

Figure 34:
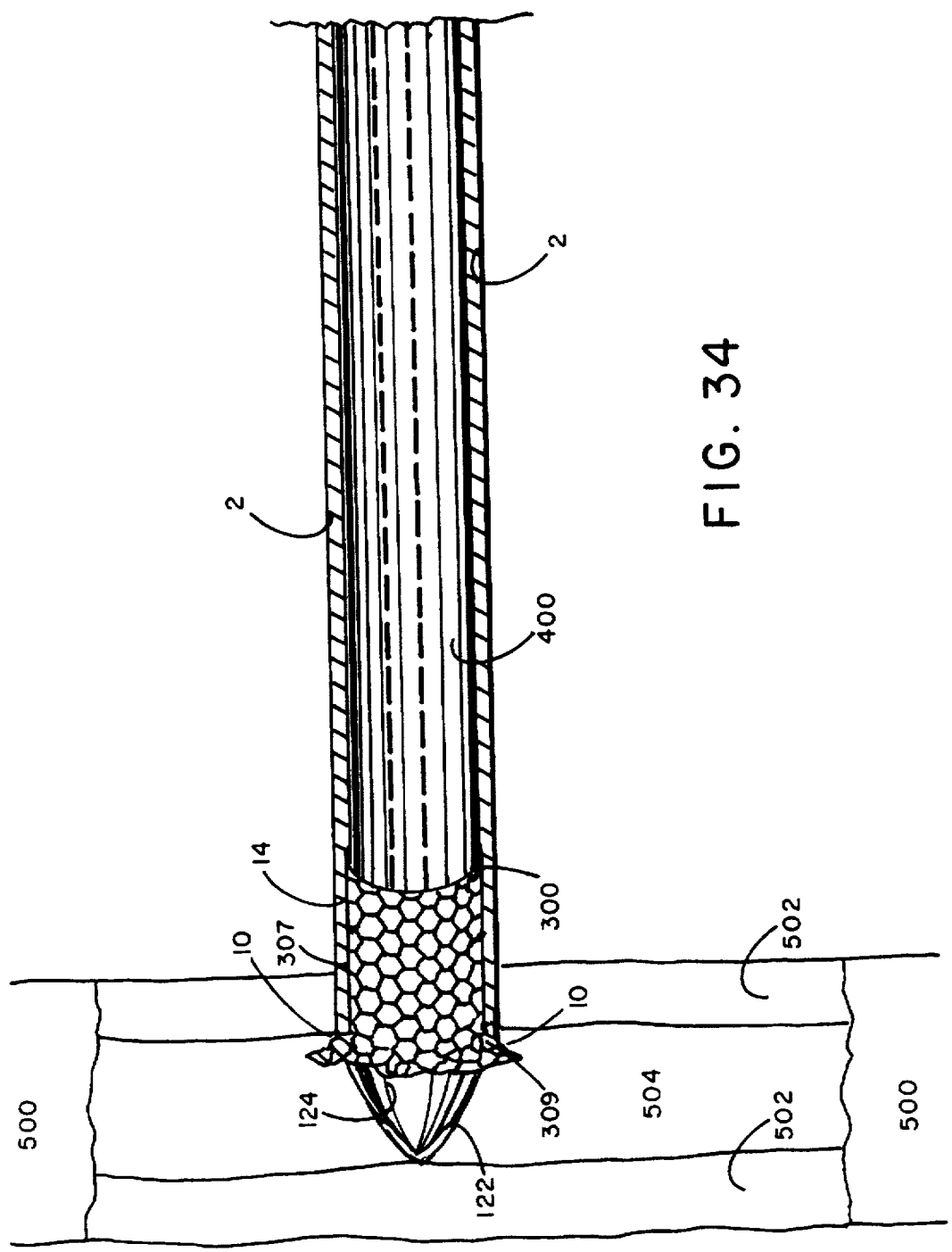
FIG. 34 is a partially exposed view of the engaged cuff beginning thermal deformation in-situ while being extended into the internal lumen of the unobstructed blood vessel in-vivo.

FIG. 34 also shows that the puncturing headpiece 122 has been reduced in overall size and shows a diminished diameter or girth in comparison to its initial size as shown previously via FIGS. 30–33 respectively. The reduced overall size and altered configuration of the puncturing headpiece 122 lying disposed within the arterial lumen in-vivo is a preferred manipulation of the methodology provided by the use of variable-size obturators.

Alternatively, the puncturing headpiece 122 may be fixed in both size and shape; and the thermally deforming sidewall of the cuff 300 will be made to expand outwardly along its length in order to allow the fixed-size puncturing headpiece to pass through the outwardly expanded cuff diameter. Also, the outward expansion by the deformed cuff can improve and enhance watertightness between the cuff 300 and the arterial wall 502.

After the puncturing headpiece has been desirably reduced in overall size and has a diminished girth, the overall diameter of the contracted puncturing headpiece 122 is smaller in overall size than the diameter of the thermally deformable cuff disposed directly behind the headpiece. Due to the reduced size of the puncturing headpiece 122, the thermally deforming cuff and engaged vascular segment carried upon the elongated shaft 134 of the obturator may then be controllably and completely released by withdrawing the distal end 10 of the catheter from the warm temperature environment of the arterial lumen 504. This manipulation and result is illustrated in FIGS. 34 and 35.

Figure 35:
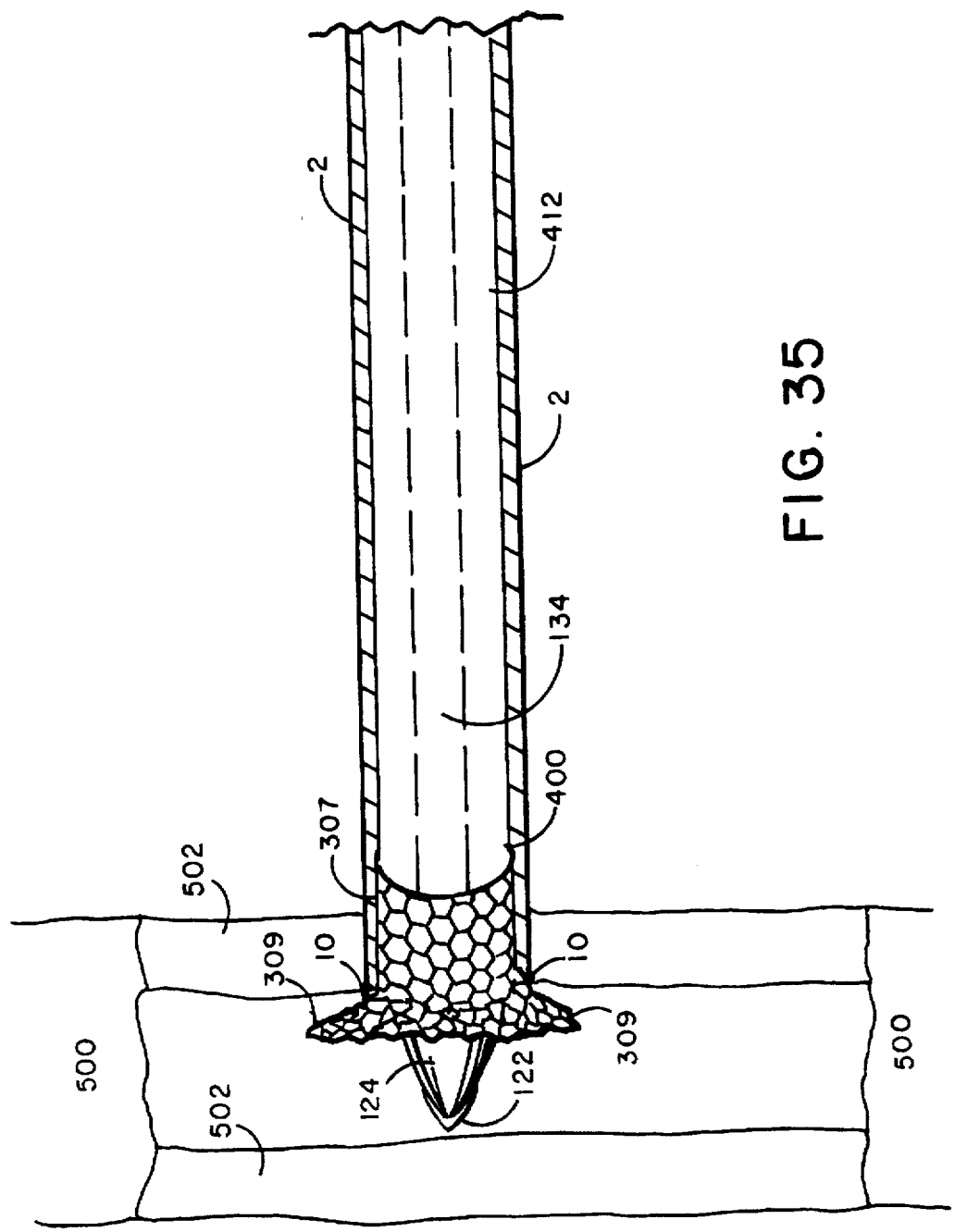
FIG. 35 is a partially exposed view of the engaged cuff continuing thermal deformation within the internal lumen of the unobstructed blood vessel in-vivo.

It is important to recognize and note that a meaningful portion of the upper sidewall of the thermoelastic cuff 300 has been released out of the catheter lumen into the arterial lumen 504 as illustrated by FIG. 35. Concomitant with the controlled release of the thermoelastic cuff 300 into the arterial lumen 504, two consequential events also occur: (a) the engaged and joined vascular segment 400 is concurrently placed and fitted into the enlarged puncture or hole in the arterial wall 502 at the chosen site; and (b) the upper sidewall portion 309 of the cuff, as it is freed from the confinement of the internal lumen of the catheter and placed in a warm temperature environment above 35° C., begins to deform thermally into the memory-shaped second configuration.

The degree of extension and rate at which the engaged cuff and the vascular segment is controllably released from the catheter lumen lies at the discretion of the surgeon performing this methodology. If the surgeon so chooses, the deformable cuff and the excised vascular segment may be extended through the thickness of the arterial wall but not far or completely into the arterial lumen itself. In the alternative, the surgeon may choose to advance the engaged cuff and vascular segment extensively or completely and thus position the upper sidewall portion of the cuff as far as possible within the internal lumen of the artery itself. The degree of entry as well as the rate of release of the deformable cuff and the engaged vascular segment into the warm temperature environment above 35° C. of the arterial lumen thus is the choice and judgment of the surgeon at all times.

Figure 36:
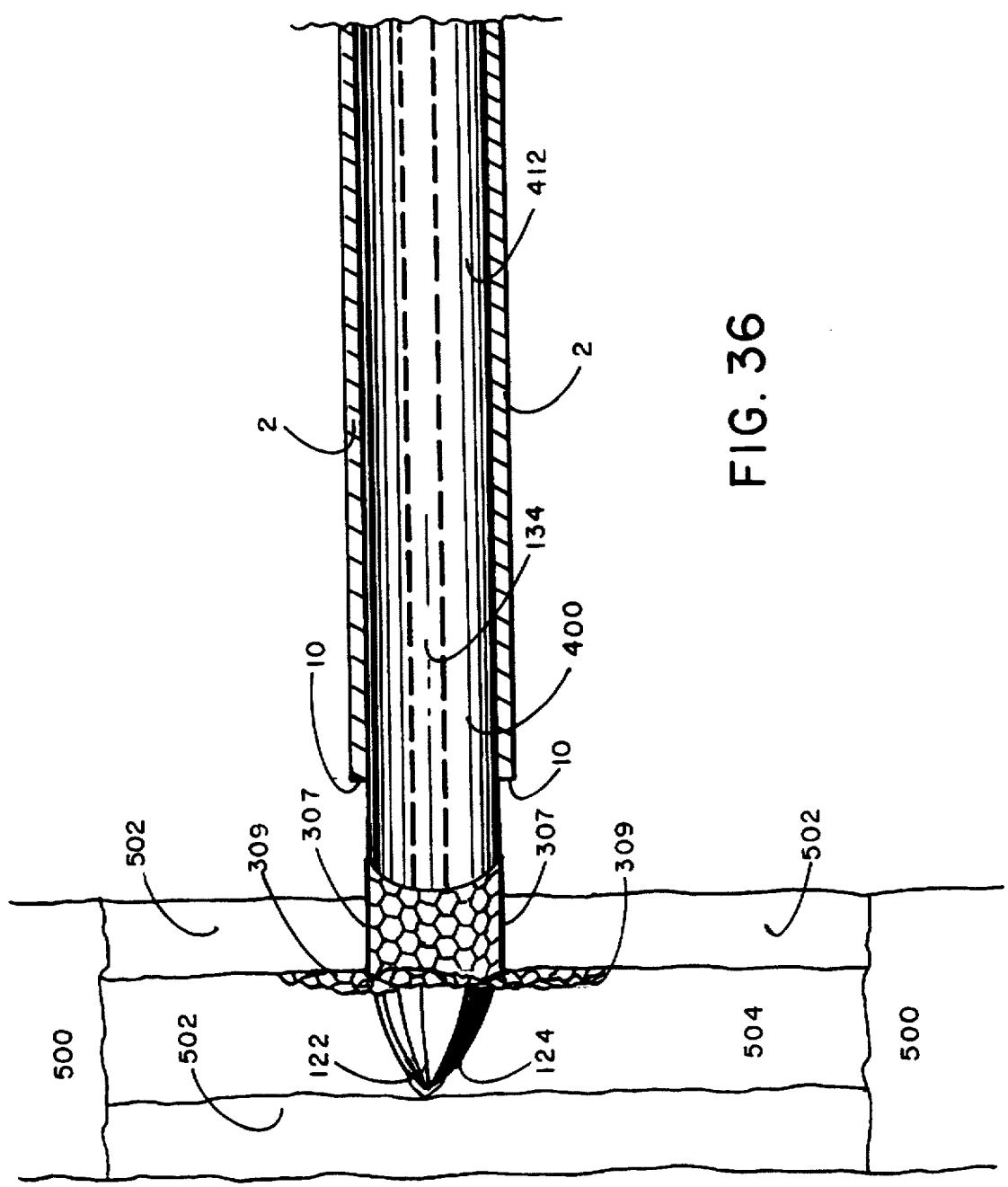
FIG. 36 is a partially exposed view of the puncturing headpiece in the secondary contracted state after thermal deformation of the cuff in-situ within the internal lumen of the unobstructed blood vessel in-vivo.

After the thermoelastic cuff 300 and the engaged vascular segment 400 have been advanced such that each has penetrated the arterial wall 502 and at least a portion of the upper sidewall 309 of the deformable cuff 300 has been released into the arterial lumen, to the surgeon's personal discretion and accommodation, the uppermost region 309 of the deformable cuff 300 will thermally deform in-situ into the memory-shaped second configuration—as shown by FIG. 36. The warm temperature environment above 35° C. of the arterial lumen has caused the upper sidewall 309 of the cuff to deform in-situ; to become bent outwardly; and to become flaired and flattened out within the internal lumen 504 of the artery 500. Then, as the memory-shaped second configuration for the cuff appears in an ever greater degree, the sidewall 309 of the cuff 300 will become more flattened; will come to lie substantially against the interior surface of the arterial wall 502; and will become secured to the arterial wall in a permanent manner. This consequence and result is also illustrated by FIG. 36.

The controlled thermal deformation and flairing of the uppermost sidewall 309 of the cuff 300 occurs in-situ within the warm, blood flow channel of the artery and the act of controlled deformation is performed without substantially diminishing the rate of blood through the lumen of the artery or causing the heart of the patient to stop at any time. The intentional and controlled thermal deformation of the cuff along its upper sidewall as it lies disposed within the arterial lumen causes a permanent flairing of the open meshwork of wires forming the sidewall. The deformed sidewall is bent, maneuvered, and flaired in-situ solely by the warming of the memory-shaped alloy comprising the cuff to a temperature above 35° C. No tool, article, or mechanical device is needed or utilized in order to cause a controlled deformation of the cuff while disposed within the blood channel of the artery in-vivo.

After the cuff has been thermally deformed within the arterial lumen 504 and become secured to the interior surface of the arterial wall 502 to the personal satisfaction of the surgeon, the puncturing headpiece 122 and the obturator as a whole can be removed. The surgeon is confident that the overall diameter of the contracted puncturing headpiece is smaller than the diameter of both the cuff and the engaged vascular segment; and therefore, the puncturing headpiece will then be able to enter and pass completely through the fully deformed cuff and the internal lumen of the engaged vascular segment in-situ without meaningfully injuring or altering the internal surface of the blood flow channel itself.

Figure 37:
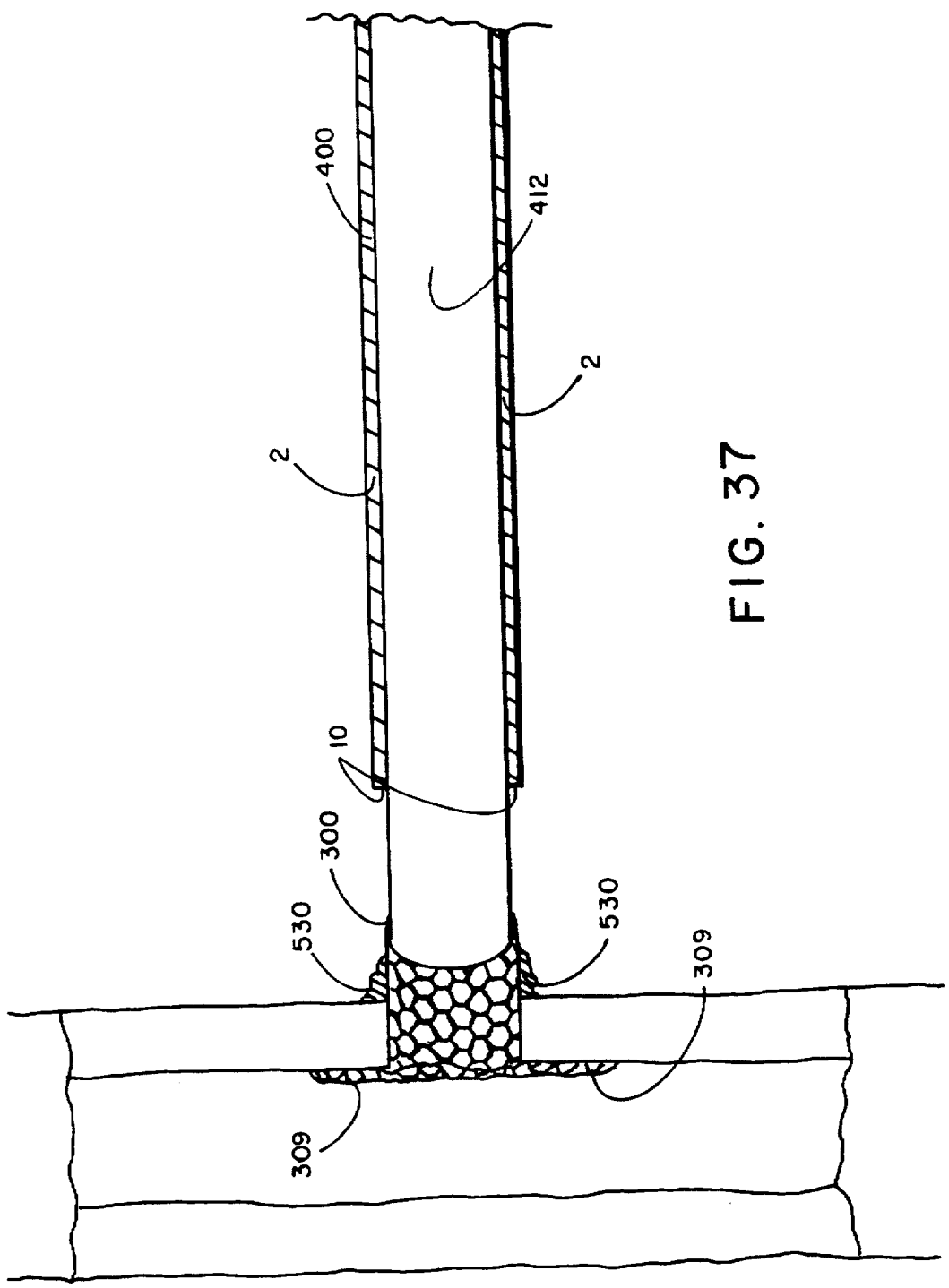
FIG. 37 is a partially exposed view of the thermally deformed cuff and vascular segment secured fluid-tight to and in blood flow communication with the internal lumen of the unobstructed blood vessel in-vivo.

The act of removing the obturator is quickly accomplished by the skilled surgeon; and the act of removal serves to isolate the now fully deformed sidewall 309 of the cuff 300 secured to the interior surface of the arterial wall 502. The deformed cuff 300 and the engaged vascular segment 400 remain permanently secured and attached to the blood flow channel of the major artery in a manner which permits arterial blood to enter through the deformed cuff into the internal lumen of the vascular segment without meaningful major alteration of the primary artery and without major destruction of vascular tissues at the site of graft bypass juncture. To ensure that the placement of the deformed cuff and engaged vascular segment is fluid-tight, the surgeon then preferably applies a biocompatible adhesive 530 to the exterior surface of the arterial wall 502 at the puncture site. The biocompatible adhesive 530 is desirably spread over the sidewall 306 of the cuff 300 at the exterior surface of the arterial puncture site. This act and result is shown by FIG. 37. The applied biocompatible adhesive dries quickly; forms a permanent and fluid-tight seal at the puncture site; and will not degrade or cause irritation to either the artery wall or the grafted vascular segment now to be used as a bypass conduit. Note also that the catheter has desirably also been removed prior to the placement of the biocompatible adhesive at the puncture site on the arterial wall. This catheter removal step is preferred in order to have better access to the thermally deformed cuff at the point of juncture.

A number of different biocompatible adhesives may be employed to seal permanently the puncture site in the manner shown by FIG. 37. A representative but non-exhaustive listing of such biocompatible adhesives is provided by Table 6 below.

TABLE 6

Biocompatible Adhesives

Adhesives Materials

Fibrin glue;
Histacryl (butyl-2-cyanoacrylate) tissue adhesive;
Cyanoacrylates;
Liquid silicones;
Epoxy resins; and
Polyurethane adhesives.

---

The overall result of this procedure is illustrated by FIG. 37 in which the uppermost region 309 of the cuff sidewall has been thermally deformed in-situ and become flaired outwardly into the internal lumen 504 of the artery 500. The open meshwork of wires 308 has aided and assisted the ease and speed by which the deformed sidewall 309 has been bent, become extended into the internal arterial lumen, and become secured in-situ to the interior surface of the arterial wall 502. Also, the placement of the biocompatible adhesive 530 at the puncture and graft juncture site places the bypass conduit in a fluid-tight setting permanently such that the engaged vascular segment 400 is attached to and is in blood flow communication with the arterial blood in an unobstructed manner. The placement and securing of the vascular bypass conduit to the major unobstructed artery is thus complete in all respects.

The other end of the excised vascular segment 400 typically is then conventionally attached to the obstructed blood vessel at a chosen site distal to the obstruction itself as illustrated by FIG. 39. The manner of joining the second open end of the grafted vascular segment to the obstructed artery or vein may be achieved conventionally by anastomosis; with or without sutures; and with or without use of tissue adhesives by the surgeon. It will be noted and appreciated also, that the surgeon, at his option, may in fact intentionally create an aperture in the wall of the grafted vascular segment 400; introduce the obturator 120 into the internal lumen of the vascular segment; place a second deformable cuff 300 in proper position; and then engage the cuff to the second open end of the vascular segment in the manner described previously. If the surgeon so chooses, therefore, the entirety of the introducer system and the catertization methodology may be repeated for use at the chosen site on the obstructed blood vessel. Nevertheless, it is generally expected that in most instances, the surgeon will prefer to perform conventional anastomosis as the means for joining the other open end of the blood vessel segment to the obstructed artery or vein. This is illustrated by FIG. 39.

The entire catheterization methodology for creating a vascular bypass graft or shunt has been shown and described in detail via FIGS. 32-39 inclusive. Each essential manipulation or required act has been illustrated in detail and described in depth. Nevertheless, to assure a complete and comprehensive presentation of the methodology as a whole, a summary recitation of the preferred surgical procedures using the catheter apparatus, the introducer system, and the methodology is provided hereinafter.

VI. SUMMARY OF THE PREFERRED SURGICAL PROCEDURES USING THE CATHETER APPARATUS AND METHOD

The catheter apparatus and methodology comprising the present invention provides an approach designed to allow surgeons do multiple bypass using vein bypass grafts in a minimally invasive way. This procedure allows a simpler way to place the vein grafts proximally to the aorta and distally to the coronary artery without using a heart-lung machine and without need for stopping the heart. Small incisions are first made between the ribs; a video camera and instruments with long handles are inserted; and, under the direct visualization, the aorta is punctured to create a proximal graft to anastomosis (aortotomy) using a specially prepared catheter introducer system which internally carries a deformable cuff and a previously excised vascular segment.

The thermally deformable cuff is made of nickel-titanium alloy wire mesh; and is preferably coated with prosthetic material such as PTFE. The cuff will become anchored by thermal deformation at a temperature above about 35° C. inside the aortic wall and be secured and blood-leak-proven outside the aortic wall by subsequently applying a tissue adhesive. This thermally deformed cuff will provide a secure sutureless aortic anastomosis for the bypass vein graft. The proximal part of the vein graft is preferably sewn to the cuff. The bypass graft is then distally anastomosed to the coronary artery, which can be done either by the conventional way with sutures or by applying tissue adhesive between the adjacent outer walls of the bypassable coronary artery and the bypass vein graft without sutures.

This unique procedure simplifies the complexity of the conventional coronary artery bypass surgery and makes the surgery less invasive. Moreover, this technique provides a critical advantage over the conventional bypass surgery (using excised vein grafts), or the thoracoscopic minimally invasive surgery (using an internal mammary vein graft). Also, it will shorten the operation time and make the coronary bypass surgery safer and more cost-effective.

Thoracotomy and Aorotocoronary Bypass

After cutting through the muscle and other tissue of the anterior chest, the surgeon separates a rib from the breast bone and cuts a piece of the cartilage at the detached end to provide working space for the aortotomy and placement of the proximal graft anastomosis.

The bypassing of the vascular blockage increases blood flow to the heart. The optimal environment for the vascular anastomosis is a motionless, dry field. In conventional coronary bypass surgery, this environment can be obtained by total cardiopulmonary bypass and cardioplegia techniques to arrest the heart. However, in minimally invasive coronary bypass surgery, it is performed without cardiopulmonary bypass and without stopping the heart. Instead, the heart beat is slowed down with cardiac medications such as calcium channel blockers and beta-blockers, and with hypothermia.

Creation of the proximal anastomosis

The ascending aorta is first palpated before creation of the aortotomy to determine the proper location of the aorta for aortotomy and delivery of the introducer system. The ascending aorta is preoperatively evaluated by means of CT scan or MRI to exclude the patient with severe atherosclerosis of the aorta, which may interfere with creation of the aorotomy and increase possible associated complications such as dissection and embolization of the plaques. When the ascending aorta is shown to be moderately thick by CT or MRI, the deformable cuff is larger (7 to 8 mm outer diameter) than usual (5 to 6 mm outer diameter) and may be placed in the aorta to prevent narrowing at the proximal anastomosis.

This technique involves safe and simple placement of the proximal anastomosis of the vein graft without clamping of the aorta and without using heart-lung machine. The proximal part of the ascending thoracic aorta is first exposed and punctured with an obturator that carries a cuff and a previously excised blood vessel segment within it (FIGS. 31–33). The cuff is made of a nitinol wire mesh; and will thermally deform into a memory-shaped flared end which will become firmly anchored against the inner wall of the thoracic aorta. The cuff is desirably covered with a prosthetic material (such as Dacron and PTFE, etc.) to prevent any leaking of blood through the mesh cuff. Continuous 5-0 Prolene is used for the anastomosis between the cuff and the grafts when the saphenous vein is the usual size (5 to 6 mm).

After the aortic puncture, the proximal end of the cuff vein graft is thermally deformed as it is released into the arterial lumen. The obturator is then retracted and the vein graft is slowly pulled back until the cuff is anchored and secured against the internal wall of the aorta via its deformed flared end. Once the cuff and the proximal end of the vein graft is internally anchored, the catheter and obturator are removed; and tissue adhesive (glue) is applied around the exit site of the bypass graft (between the graft and the adjacent outer wall of the aorta) so that any possibility of leakage of blood will be minimized and also to secure further the proximal anastomosis. The upper end of the vein graft is clamped to stop blood flow; and drugs are injected into the lower end to prevent it from going into spasm while the surgeon works on the coronary anastomosis.

Exposure of the coronary arteries and creation of the distal anastomosis

The sac covering the heart is cut, the thin coronary artery is under direct view. The patient is given calcium channel blockers and a beta blocker intravenously to slow the heart, which facilitate that the surgeons thread the stitches through the artery. The coronary artery vessels to be bypassed is identified and exposed after opening either hemithorax.

With a sharp knife, the surgeons cut into the coronary artery (arteriotomy). The arteriotomy is then increased to 8 to 12 mm with Pott's or reversed acute angle scissors. The internal diameter of the coronary artery is calibrated and the size recorded. The distal part of the graft that has been set aside is sewn to the coronary artery with the same fine sutures that are used in standard bypass operations. A continuous suture of 6-0 or 7-0 Prolene is begun in the heel of the vein graft with a narrow mattress stitch and continued to the proximal portion of the coronary artery. Approximately 1-mm bites are taken as the suture line is continued around one side to the distal end. At that point the suture line may be interrupted with one or more sutures. With smaller vessels interrupted sutures are easy to insert and less likely to constrict the anastomosis. With larger vessels (2.5 mm or greater) the suture line may be continued without interruption around the distal end. The other end of the original stitch is continued on the contralateral side, and the anastomosis is terminated at the midpoint of the arteriotomy. Anastomotic patency is checked in both directions. A flush of clear solution through the needle may be of aid during the performance of the distal anastomosis to keep the anastomotic area free of blood. Alternatively, the coronary artery and bypass vein grafts can be anastomosed by applying tissue adhesive (glue) between their adjacent outer walls, without using sutures, which facilitates and expedites the coronary anastomosis. when application of tissue adhesive make two structures bonded in a side-to-side fashion, a fenestration in a proper length is made between them by putting an incision extending from the lumen of vein graft to the lumen of the coronary artery with a knife inserted via the distal open end of the graft. After this, the open distal end of the vein graft is sewn as a blind end.

This procedure is repeated until all the blocked vessels to be revascularized are bypassed. After checking for bleeding, the surgeon closes the chest.

The present invention is not to be limited in scope nor restricted in form except by the claims appended hereto.

What I claim is:

1. A catheter apparatus for creating a bypass on-demand between an unobstructed blood vessel and an obstructed blood vessel in-vivo using a graft segment as a conduit, said bypass catheter apparatus comprising:

a catheter suitable for introduction into and extension through the body in-vivo to a chosen site wherein an unobstructed blood vessel is in anatomic proximity to an obstruction lying within another blood vessel, said catheter being comprised of a hollow tube of fixed axial length having a proximal end, a distal end, and at least one internal lumen of predetermined diameter;

an obturator for on-demand introduction and passage through said catheter to a chosen site on the unobstructed blood vessel in-vivo, said obturator comprising (1) a puncturing headpiece for puncture of and entry into the lumen of an unobstructed blood vessel, (2) a perforating end tip on said puncturing headpiece to facilitate the perforation of a blood vessel wall at the chosen site in-vivo, (3) an elongated shaft of fixed axial length integrated with said puncturing headpiece, said elongated shaft being configured for the carrying and transport of a graft segment within said internal lumen of said catheter to the chosen site on the unobstructed blood vessel in-vivo; and a thermoelastic deformable cuff comprised of a prepared shape-memory allow for positioning over said elongated shaft adjacent to said puncturing headpiece of said obturator together with a graft segment (i) wherein, prior to the perforation of the unobstructed blood vessel in-vivo by said puncturing headpiece of said obturator, a portion of said cuff in a first shaped configuration has been engaged and joined to one end of the graft segment then carried by said elongated shaft of said obturator thereby forming an engaged cuff portion and a non-engaged cuff portion, (ii) and wherein, after the perforation of the unobstructed blood vessel in-vivo by said puncturing headpiece of said obturator, at least part of said non-engaged cuff portion is extended into the lumen of the unobstructed blood vessel and becomes thermoelastically deformed in-situ into a prepared memory-shaped second configuration, and said prepared memory-shaped second configuration of said deformed non-engaged cuff portion becomes disposed onto an interior surface of the unobstructed blood vessel, (iii) and whereby said cuff engaged end of the graft segment become secured to and placed in blood flow communication with the unobstructed blood vessel and serves as a conduit means for bypassing an obstruction and restoring blood flow from the unobstructed blood vessel to the obstructed blood vessel to the obstructed blood vessel.

2. The catheter apparatus as recited in claim 1 wherein said thermally deformable cuff is comprised of a nickel-titanium alloy.

3. The catheter apparatus as recited in claim 1 wherein said thermally deformable cuff is overlaid with a biocompatible coating.

4. The catheter apparatus as recited in claim 1 wherein said thermally deformable cuff comprises an open meshwork.

5. The catheter apparatus as recited in claim 1 wherein said thermally deformable cuff comprises a solid mass of material.

6. The catheter apparatus as recited in claim 1 wherein said obturator further comprises means for expansion and contraction of said puncturing headpiece on-demand.

7. The catheter apparatus as recited in claim 1 wherein said graft segment comprises a synthetic prosthetic channel section.

8. The catheter apparatus as recited in claim 1 wherein said graft segment comprises a previously excised blood vessel segment.

9. A catheterization method for creating a bypass on-demand between an unobstructed blood vessel and an obstructed blood vessel in-vivo using a graft segment as a conduit, said bypass catheterization method comprising the steps of:

providing a catheter suitable for introduction into and extension through the body in-vivo to a chosen site wherein an unobstructed blood vessel is in anatomic proximity to an obstruction lying within another blood vessel, said catheter being comprises of a hollow tube of fixed axial length having a proximal end, a distal end, and at least one internal lumen of predetermined diameters;

providing an obturator for on-demand introduction and passage through said catheter to a chosen site on the unobstructed blood vessel in-vivo, said obturator comprising (1) a puncturing headpiece for puncture of and entry into the lumen of an unobstructed blood vessel, (2) a perforating end tip on said puncturing headpiece to facilitate the perforation of a blood vessel wall at the chosen site in-vivo, and (3) an elongated shaft of fixed axial length integrated with said puncturing headpiece, said elongated shaft being configured for the carrying and transport of a graft segment within said internal lumen of said catheter to the chosen vascular site on the unobstructed blood vessel;

placing a graft segment on the elongated shaft adjacent to said puncturing headpiece of said obturator;

positioning a thermoelastic determable cuff comprised of a prepared shape-memory alloy for positioning over said elongated shaft and an end of said graft segment lying adjacent to said puncturing headpiece of said obturator such that at least a portion of said cuff in a first configuration engages and is joined to one end of said graft segment thereby forming an engaged cuff portion and a non-engaged cuff portion;

perforating the unobstructed blood vessel at the chosen site in-vivo using said puncturing headpiece of said obturator;

extending at least part of said non-engaged cuff portion into the lumen of the unobstructed blood vessel;

allowing said extended non-engaged cuff portion to deform thermoelastically in-situ into a prepared memory-shaped second configuration within the lumen of the unobstructed blood vessel, (i) whereby said prepared memory-shaped second configuration of said deformed non-engaged cuff portion becomes disposed onto an interior surface of the unobstructed blood vessel, (ii) and whereby said cuff engaged end of said graft segment become secured to and placed in blood flow communication with the unobstructed blood vessel; and joining the other end of said secured graft segment to the obstructed blood vessel at a chosen site distal to the obstruction, said joined graft serving as means for bypassing the obstruction and restoring blood flow from the unobstructed blood vessel to the obstructed blood vessel.

10. The catheterization method as recited in claim 9 wherein the bypass conduit is created between an unobstructed artery and an obstructed artery.

11. The catheterization method as recited in claim 9 wherein the bypass conduit is created between an unobstructed vein and an obstructed vein.

12. The catheterization method as recited in claim 9 wherein the bypass conduit is created between an artery and a vein.

* * * * *